US009526709B2

(12) United States Patent
Wanebo

(10) Patent No.: US 9,526,709 B2
(45) Date of Patent: Dec. 27, 2016

(54) COMPOSITIONS AND METHODS FOR TREATING CANCER

(75) Inventor: Harold J. Wanebo, Bristol, RI (US)

(73) Assignee: Chemo-Enhanced LLC, Woonsocket, RI (US)

( * ) Notice: Subject to any disclaimer, the term of this patent is extended or adjusted under 35 U.S.C. 154(b) by 583 days.

(21) Appl. No.: 14/110,318

(22) PCT Filed: Apr. 4, 2012

(86) PCT No.: PCT/US2012/032143
§ 371 (c)(1),
(2), (4) Date: Dec. 23, 2013

(87) PCT Pub. No.: WO2012/138739
PCT Pub. Date: Oct. 11, 2012

(65) Prior Publication Data
US 2014/0105969 A1    Apr. 17, 2014

Related U.S. Application Data

(60) Provisional application No. 61/472,266, filed on Apr. 6, 2011.

(51) Int. Cl.
| A61K 31/164 | (2006.01) |
| A61K 31/555 | (2006.01) |
| A61K 31/282 | (2006.01) |
| A61K 31/435 | (2006.01) |
| A61K 9/127  | (2006.01) |
| A61K 45/06  | (2006.01) |
| A61K 31/337 | (2006.01) |
| A61K 31/365 | (2006.01) |

(52) U.S. Cl.
CPC .......... *A61K 31/164* (2013.01); *A61K 9/127* (2013.01); *A61K 31/337* (2013.01); *A61K 31/365* (2013.01); *A61K 45/06* (2013.01)

(58) Field of Classification Search
CPC .. A61K 31/164; A61K 31/282; A61K 31/555; A61K 31/435; A61K 45/05; A61K 9/0019; A61K 9/127
IPC .................................................... A61K 31/164
See application file for complete search history.

(56) References Cited

U.S. PATENT DOCUMENTS

| 7,015,251 | B1 | 3/2006 | Wanebo et al. |
| 7,820,718 | B1 | 10/2010 | Wanebo et al. |
| 8,216,607 | B2 | 7/2012 | Wanebo |
| 2005/0249795 | A1* | 11/2005 | Zhang .................. A61K 9/1272 424/450 |

(Continued)

FOREIGN PATENT DOCUMENTS

| WO | WO-00/59517 | A1 | 10/2000 |
| WO | 2007/143175 |  * | 12/2007 |

(Continued)

OTHER PUBLICATIONS

Beiner, M.E., et al, Int. Gynecol. Cancer, 16 (Suppl. 1), pp. 200-206, 2006.*

(Continued)

*Primary Examiner* — Gollamudi Kishore
(74) *Attorney, Agent, or Firm* — Foley Hoag LLP

(57) ABSTRACT

The present invention provides, in part, compositions and methods for treating cancer using a combination of C6-ceramide and other anti-cancer agents.

4 Claims, 7 Drawing Sheets

C6 Ceramide sensitizes Taxol and Gemcitabine induced pancreatic cancer cell death by AMPK activation and PI3K/AKT/mTOR in-activation.

(56) References Cited

U.S. PATENT DOCUMENTS

| | | |
|---|---|---|
| 2008/0033039 A1 | 2/2008 | Wanebo |
| 2008/0058274 A1* | 3/2008 | Barenholz ............ A61K 9/1272 514/34 |
| 2009/0042810 A1 | 2/2009 | Chung |
| 2009/0246271 A1 | 10/2009 | Wanebo |
| 2009/0286847 A1 | 11/2009 | Fang et al. |

FOREIGN PATENT DOCUMENTS

| | | |
|---|---|---|
| WO | WO-2007/143175 A2 | 12/2007 |
| WO | WO-2012/088414 A1 | 6/2012 |

OTHER PUBLICATIONS

Roock et al, JAMA, vol. 304, No. 15, pp. 1812-1820, 2010.*
Zundelevich, A., et al, Mol. Cancer Ther. 6 (6), pp. 1765-1773.*
Trosko, J.E., Mutation Research, 480-481, pp. 219-229, 2001).*
Voskoglou-Nomolkos, T., Clinial Cancer Research, vol. 9, pp. 4227-4239, 2003.*
Arlt et al., "Role of NF-κB and Akt/PI3K in the resistance of pancreatic carcinoma cell lines against gemcitabine-induced cell death," Oncogene, 22:3243-3251 (2003).
Garassino et al., "Different types of K-Ras mutations could affect drug sensitivity and tumour behaviour in non-small-cell lung cancer," Annals of Oncology, 22(1):235-237 (2011).
Guo et al., "The AMPK agonist AICAR inhibits the growth of EGFRvIII-expressing glioblastomas by inhibiting lipogenesis," PNAS, 106(31):12932-12937 (2009).
International Search Report dated Sep. 21, 2012, from PCT/US12/32143.
Ji et al., "Exogenous cell-permeable C6 ceramide sensitizes multiple cancer cell lines to Doxorubicin-induced apoptosis by promoting AMPK activaction and mTORC1 inhibition," Oncogene, 29:6557-6568 (2010).
Liu et al., "Compartmentalized Production of Ceramide at the Cell Surface," The Journal of Biological Chemistry, 270 (45):27179-27185 (1995).
Mehta et al., "Combined cytotoxic action of paclitaxel and ceramide against the human Tu138 head and neck squamous carcinoma cell line," Cancer Chemother. Pharmacol., 46:85-92 (2000).
Myrick et al., "Paclitaxel-induced apoptosis in Jurkat, a leukemic T cell line, is enhanced by ceramide," Leukemia Research, 23:569-578 (1999).
Pollastri et al., "Synthesis, structure, and thermal properties of 1,2-dipalmitoylgalloylglycerol (DPGG), a novel self-adhering lipid," Chemistry and Physics of Lipids, 104:67-74 (2000).
Poplin et al., "Phase III, Randomized Study of Gemcitabine and Oxaliplatin Versus Gemcitabine (fixed-dose rate infusion) Compared With Gemcitabine (30-minute infusion) in Patients With Pancreatic Carcinoma E6201: A Trial of the Eastern Cooperative Oncology Group," Journal of Clinical Oncology, 27(23):3778-3785 (2009).
Qiu et al., "Paclitaxel and ceramide synergistically induce cell death with transient activation of EGFR and ERK pathway in pancreatic cancer cells," Oncology Reports, 16:907-913 (2006).
Ray et al., "Epithelial Tissues Have Varying Degrees of Susceptibility to $Kras^{G12D}$-Initiated Tumorigenesis in a Mouse Model," PLoS One, 6(2):e16786 (2011).
Roock et al., "Association of KRAS p. G13D Mutation With Outcome in Patients With Chemotherapy-Refractory Metastic Colorectal Cancer Treated with Cetuximab," JAMA, 304(16):1812-1820 (2010).
Roth et al., "Prognostic Role of KRAS and BRAF in Stage II and III Resected Colon Cancer: Results of the Translational Study on the PETACC-3, EORTC 40993, SAKK 60-00 Trial," Journal of Clinical Oncology, 28(3):466-474 (2010).
Shrayer et al., "Apoptosis signal ceramide c6 synergizes anti-tumor effects of paclitaxel oxaliplatin & cisplatin on growth of pancreatic cancer in SCID mice," Journal of Clinical Oncology, ASCO, 24(18S) (2006) Abstract 13135.
Shrayer et al., "Ceramide (C6) significantly augments the anti-tumor effect of paclitaxol on the engrafted L3.6 pancreatic CA," ASCO, 22:243 (2003) Abstract 972.
Stathopoulos et al., "Present Treatment and Future Expectations in Advanced Pancreatic Cancer," Anticancer Research, 28:1303-1308 (2008).
Stover et al., "Liposomal Delivery Enhances Short-Chain Ceramide-Induced Apoptosis of Breast Cancer Cells," Journal of Pharmacology and Experimental Therapeutics, 307(2):468-475 (2003).
Tettamanti et al., "Salvage pathways in glycosphingolipid metabolism," Biochimie, 85:423-437 (2003).
van Vlerken et al., "Augmentation of Therapeutic Efficacy in Drug-Resistant Tumor Models Using Ceramide Coadministration in Temporal-Controlled Polymer-Blend Nanoparticle Delivery Systems," The AAPS Journal, 12(2):171-180 (2010).
Wanebo et al., "Abstract 4767: C6 ceramide sensitizes multiple aggressive pancreatic cancer cell lines to gemcitabine, paclitaxel and cetuximab mediated anti tumor effects in vivo and in vitro," Cancer Research, 71(8):4767 Abstract (2011).
Wanebo et al., "The apoptosis signal ceramide (C6) significantly enhances the anti-tumor effects of a variety of chemo therapeutic drug classes D," Ann. Surg. Oncol., 15(S2):69 (2008) Abstract P116.
Zhu et al., "C6-ceramide synergistically potentiates the anti-tumor effects of histone deacetylase inhibitors via AKT dephosphorylation and α-tublin hyperacetylation both in vitro and in vivo," Cell Death and Disease, 2:(e117):1-12 (2011).
Zolnik et al., "Rapid Distribution of Liposomal Short-Chain Ceramide in Vitro and In Vivo," Drug Metabolism and Disposition, 36(8):1709-1715 (2008).
Modrak, D. E. et al., "Synergistic Interaction between Sphingomyelin and Gemcitabine Potentiates Ceramide-Mediated Apoptosis in Pancreatic Cancer", *Cancer Research*, 64:8405-8410 (2004).
Perabo, F. G. E., et al., "Preclinical evaluation of gemcitabine/paclitaxel-interactions in human bladder cancer lines", *Anticancer Research*, 23:4805-4814 (2003) (Abstract).
Stover, T. C. et al., "Systemic Delivery of Liposomal Short-Chain Ceramide Limits Solid Tumor Growth in Murine Models of Breast Adenocarcinoma", *Clinical Cancer Res.*, 11(9):3465-3474 (May 1, 2005).
Tolis, C. et al., "Cell Cycle Disturbances and Apoptosis Induced by Topotecan and Gemcitabine on Human Lung Cancer Cell Lines", *European Journal of Cancer*, 35(5):796-807 (1999).
Trosko, J. E. et al., "Mechanism of up-regulated gap junctional intercellular communication during chemoprevention and chemotherapy of cancer", *Mutation Research*, 480-481:291-229 (2001).

* cited by examiner

COMPOSITIONS AND METHODS FOR TREATING CANCER

RELATED APPLICATIONS

This application is the National Stage application of PCT/US12/032143, filed Apr. 4, 2012, which claims the benefit U.S. Provisional Application No. 61/472,266, filed on Apr. 6, 2011; the contents of said applications are incorporated herein in their entirety by this reference.

BACKGROUND OF THE INVENTION

Membrane sphingolipids have been shown to be biologically active and exert numerous regulatory effects on cellular functions including modulating cell growth and differentiation. Ceramides, found in high concentrations within the cell membrane, are a family of lipid molecules composed of sphingosine and a fatty acid which function as structural elements, as well as signaling molecules. Studies have demonstrated important relationships between ceramide production and apoptosis in tumor cells and suggest that processes which enhance intracellular ceramide accumulation may provide in favorable proapoptotic effects during cancer chemotherapy (Bose et al. (1995) *Cell* 82:405-414; Mathias et al. (1998) *Biochem. J.* 335 (Pt 3): 465-480). Cell permeable short chain ceramides (C2- or C6-ceramide) have shown activity relevant to therapeutically treating cancer indications. For example, such ceramide forms have an anti-cancer effect on many cancer cell lines (reviewed in Radin (2003) *Biochem. J.* 371 (Pt 2): 243-256), including melanoma and soft tissue sarcoma (Auzenne et al. (1998) *Melanoma Res.* 8:227-239), Jurkat leukemia (Myrick et al. (1999) *Leuk. Res.* 23:569-578), and head and neck squamous cancer (Mehta et al. (2000) *Cancer Cheother. Pharmacol.* 46:85-92) cell lines. Ceramides C2, C6 and their analogues have also been shown to induce cell cycle arrest in a variety of tumor types (reviewed in Mathias et al. (1998) *Biochem. J.* 335 (Pt 3): 465-480). Generation of endogenous ceramide has been shown to mediate apoptosis induced by a variety of anti-cancer drugs (reviewed in Mathias et al. (1998) *Biochem. J.* 335 (Pt 3): 465-480) including daunorubicin (Reddy et al. (2000) *J. Immunol.* 164:1355-1363), doxorubicin (Lucci et al. (1999) *Cancer* 86:300-311), ara-C (Strum et al. (1994) *J. Biol. Chem.* 269:15493-15497), suramin (Safavy et al. (2003) *Bioconjug. Chem.* 14:302-310), and paclitaxel (Charles et al. (2001) *Cancer Chemother. Pharmacol.* 47:444-450). Despite these observations, however, the molecular mechanisms underlying the therapeutically beneficial effects of ceramide, particularly cell permeable ceramides such as C6-ceramide, are unknown. This lack of understanding has hindered the development of compositions and methods containing ceramide (e.g., C6-ceramide) in combination with other agents that enhance the specific anti-cancer pathways affected by ceramide and/or overcome the pro-survival side effects of many anti-cancer therapeutics currently used in the clinic. Accordingly, there is a great need in the art to better understand the molecular mechanisms underlying the anti-cancer effect of ceramide and its derivatives.

SUMMARY OF THE INVENTION

The present invention is based, at least in part, on the discovery that the use of ceramide (e.g., C6-ceramide), in combination with one or more anti-cancer agents, e.g., a chemotherapeutic agent or EGFR inhibitor, for the treatment of certain cancers (e.g., cancers characterized by hyperactive KRAS mutant polypeptides and/or pancreatic or colorectal cancer).

In one aspect, the present invention provides a method for treating cancer, wherein the method comprises contacting a cancer cell having an activating KRAS mutation with (a) an effective amount of C6-ceramide; and (b) an effective amount of at least one anti-cancer agent, thereby treating cancer.

In another aspect, the present invention provides a method for treating cancer, wherein the method comprises contacting a cancer cell with (a) an effective amount of C6-ceramide; (b) an effective amount of an anti-cancer agent; and (c) an effective amount of an agent selected from the group consisting of an enhancer of the AMPK signaling pathway, an inhibitor of the PI3K/AKT/mTORC1 signaling pathway, and an inhibitor of the MEK/ERK signaling pathway, thereby treating cancer.

BRIEF DESCRIPTION OF THE DRAWINGS

FIG. 2B), mouse body weight (in grams) were recorded (FIG. 2E). The average rate of tumor development was calculated by total tumor volume dividing by total number of days monitored (FIG. 2C). The experiments were repeated at least three times and similar results were observed.

and tumor volume (in cm³; FIGS. 3C and 3D) were recorded (FIG. 3E). Pancreatic cancer cell lines, including L3.6 cells (FIG. 3F), Panc-1 cells (FIG. 3G) and MIA-PaCa2 cells (MIA, FIG. 3H) were cultured in basic DMEM medium and were treated with gemcitabine (Gem, 1 µg/ml). Mitomycin C was always present in the media to prevent cell proliferation from occurring. The data represent the mean±SD of at least triplicate experiments. *P<0.05 versus group without C6-ceramide presents. The experiments were repeated at least three times and similar results were observed.

DETAILED DESCRIPTION OF THE INVENTION

Figure 1:
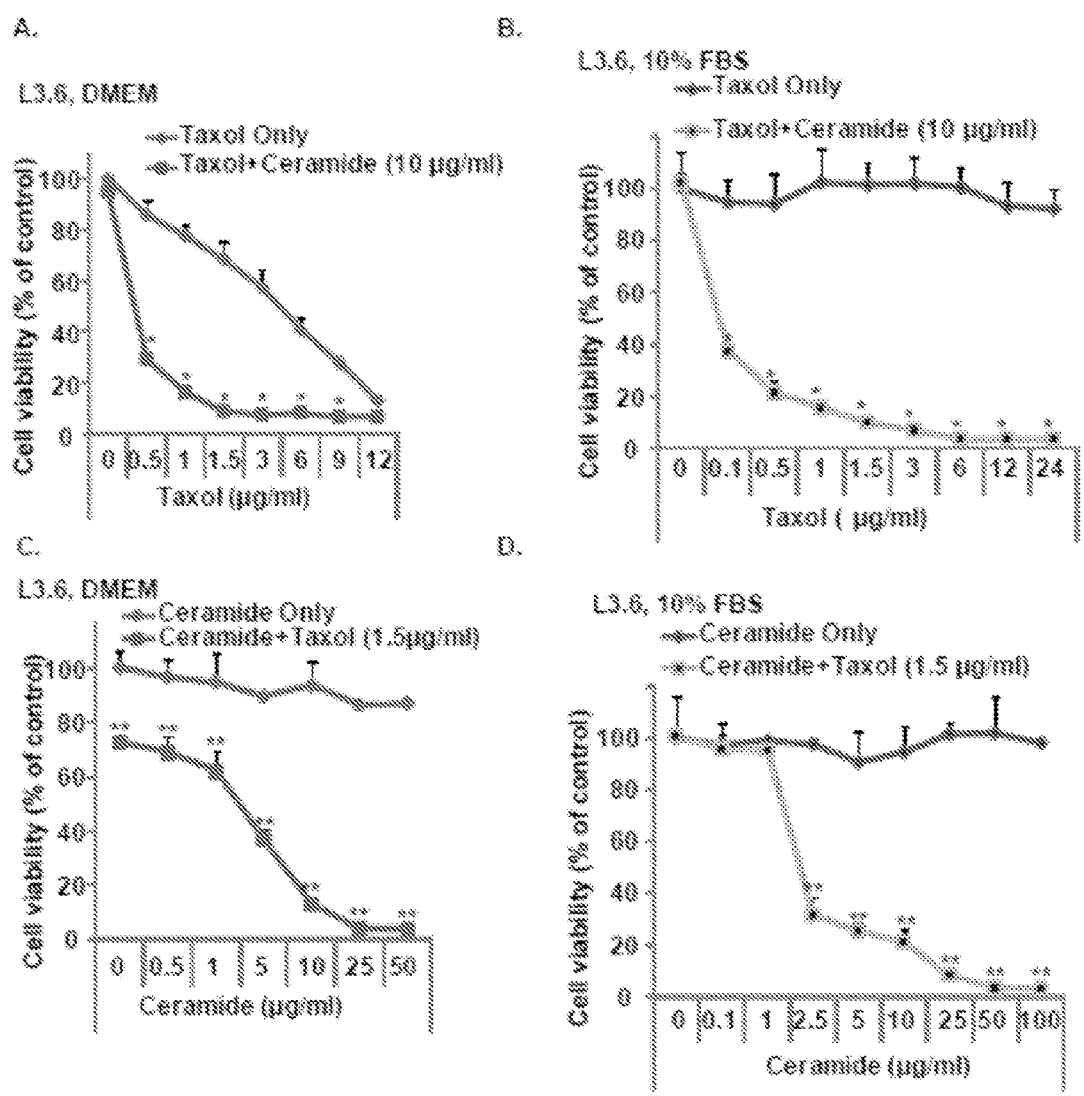
FIGS. 1A-1D show that C6-ceramide dramatically enhances taxol induced cell death in L3.6 pancreatic cancer cells in vitro. L3.6 pancreatic cancer cells, cultured either in basic DMEM medium or with 10% FBS, were treated with the indicated doses of taxol in the presence or absence of C6-ceramide (10 μg/ml) for 48 hours and cell viability was detected by MTT assay (FIGS. 1A-1B). L3.6 cells, cultured either in basic DMEM medium or with 10% FBS, were treated with the indicated dose of C6-ceramide in the presence or absence of taxol (1.5 μg/ml) for 48 hours and cell viability was detected by MTT assay (FIGS. 1C-1D). Mitomycin C (10 μg/ml) was always present in the media to prevent cell proliferation from occurring. The data represents the mean±SD of at least triplicate experiments. *P<0.05 versus group without C6-ceramide presents (FIGS. 1A-1B). **P<0.05 versus group without taxol presents (FIGS. 1C-1D).

The present invention relates to the use of ceramide (e.g., C6-ceramide), in combination with one or more anti-cancer agents, e.g., a chemotherapeutic agent, for the treatment of cancer. The present invention also relates to compositions and methods for treating certain cancers (e.g., cancers characterized by hyperactive KRAS mutant polypeptides and/or pancreatic or colorectal cancer), wherein cancer cells are contacted with an effective amount of ceramide (e.g., C6-ceramide) and an effective amount of at least one (i.e., one or more) anti-cancer agents (e.g., a chemotherapeutic agent, an enhancer of the AMPK signaling pathway, an inhibitor of the PI3K/AKT/mTORC1 signaling pathway, an inhibitor of the MEK/ERK signaling pathway, and combinations thereof).

In order that the present invention may be more readily understood, certain terms are first defined. Additional definitions are set forth throughout the detailed description.

I. Definitions

The articles "a" and "an" are used herein to refer to one or to more than one (i.e. to at least one) of the grammatical object of the article. By way of example, "an element" means one element or more than one element.

As used herein, the term "activating KRAS mutation" refers to a mutation in a KRAS polypeptide that causes enhanced KRAS activity relative to the control wild-type KRAS polypeptide without the mutation. In one embodiment, the activating KRAS mutation is selected from the group consisting of G12C; G12A; G12D; G12R; G12S; G12V; G13C; G13D of the human KRAS polypeptide. The term "altered activity" refers to an activity of a molecule (e.g., a polypeptide) which is increased or decreased in a defined state (e.g., in a mutated or diseased state and/or sample), as compared to the activity of the biomarker in a control state (e.g., in a wild type or normal, control state and/or sample). Altered activity may be the result of, for example, altered expression of the biomarker, altered protein level of the biomarker, altered structure of the biomarker, or, e.g., an altered interaction with other proteins involved in the same or different pathway as the biomarker or altered interaction with transcriptional activators or inhibitors, or altered methylation status. Such altered activity can be at least 10%, 20%, 30%, 40%, 50%, 60%, 70%, 80%, 90%, 100%, 150%, 200%, 250%, 300%, 350%, 400%, 450%, 500%, 1000%, or more modulated (e.g., upregulated or downregulated).

As used herein, the term "anti-cancer response" to therapy relates to any response of the cancer to therapy, preferably to a change in tumor mass and/or volume after initiation of neoadjuvant or adjuvant chemotherapy. Hyperproliferative disorder response may be assessed in a neoadjuvant or adjuvant situation where the size of a tumor after systemic intervention can be compared to the initial size and dimensions as measured by CT, PET, mammogram, ultrasound or palpation. Response may also be assessed by caliper measurement or pathological examination of the tumor after biopsy or surgical resection. Response may be recorded in a quantitative fashion like percentage change in tumor volume or in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment of hyperproliferative disorder response may be done early after the onset of neoadjuvant or adjuvant therapy, e.g., after a few hours, days, weeks or preferably after a few months. A typical endpoint for response assessment is upon termination of neoadjuvant chemotherapy or upon surgical removal of residual tumor cells and/or the tumor bed. This is typically three months after initiation of neoadjuvant therapy.

As used herein, the term "body fluid" refers to fluids that are excreted or secreted from the body as well as fluid that are normally not (e.g. amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, pus, saliva, sebum, semen, serum, sweat, synovial fluid, tears, urine, vaginal lubrication, vitreous humor, vomit).

As used herein, the term "cancer" is intended to encompass a tumor, including both in vitro and in vivo tumors that form in any organ or body part of the subject. Examples of the types of tumors intended to be encompassed by the present invention include those tumors associated with breast cancer, skin cancer, bone cancer, prostate cancer, liver cancer, lung cancer, brain cancer, cancer of the larynx, gallbladder, pancreas, rectum, parathyroid, thyroid, adrenal, neural tissue, head and neck, colon, stomach, bronchi, kidneys. Specifically, the tumors whose growth rate is inhibited by the present invention include basal cell carcinoma, squamous cell carcinoma of both ulcerating and papillary type, metastatic skin carcinoma, osteo sarcoma, Ewing's sarcoma, veticulum cell sarcoma, myeloma, giant cell tumor, small-cell lung tumor, gallstones, islet cell tumor, primary brain tumor, acute and chronic lymphocytic and granulocytic tumors, hairy-cell tumor, adenoma, hyperplasia, medullary carcinoma, pheochromocytoma, mucosal neuromas, intestinal ganglloneuromas, hyperplastic corneal nerve tumor, marfanoid habitus tumor, Wilm's tumor, seminoma, ovarian tumor, leiomyomater tumor, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumor, polycythermia vera, adenocarcinoma, glioblastoma multiforma, leukemias, lymphomas, malignant melanomas, epidermoid carcinomas, and other carcinomas and sarcomas.

In one embodiment, the cancer is pancreatic cancer. The term "pancreatic cancer" as used herein, includes adenomas, adenocarcinomas, gastrinomas, somatostatinomas, insulinomas and glucagonomas of the pancreas. As used herein, the term "adenocarcinoma" is carcinoma that develops in the lining or inner surface of an organ and is derived from glandular tissue or in which the tumor cells form recognizable glandular structures. As used interchangeably herein, the terms, "pancreatic adenocarcinoma," or "pancreatic ductal adenocarcinoma" is an adenocarcinoma of the pancreas. In one embodiment, pancreatic adenocarcinomas arise from the progression of lesions that occur in the pancreatic ducts (pancreatic intraepithelial neoplasia, referred to herein as "PanIN"). Pancreatic cancer is a malignant growth of the pancreas that mainly occurs in the cells of the pancreatic ducts. This disease is the ninth most common form of cancer, yet it is the fourth and fifth leading cause of cancer deaths in men and women, respectively. Cancer of the pancreas is almost always fatal, with a five-year survival rate that is less than 3%. The most common symptoms of pancreatic cancer include jaundice, abdominal pain, and weight loss, which, together with other presenting factors, are nonspecific in nature. Thus, diagnosing pancreatic cancer at an early stage of tumor growth is often difficult and requires extensive diagnostic work-up, often times including exploratory surgery. Endoscopic ultrasonography and computed tomography are the best noninvasive means available today for diagnosis of pancreatic cancer. However, reliable detection of small tumors, as well as differentiation of pancreatic cancer from focal pancreatitis, is difficult. The vast majority of patients with pancreatic cancer are presently diagnosed at a late stage when the tumor has already extended outside of the capsule to invade surrounding organs and/or has metastasized extensively (Gold et al. (2001) *Crit. Rev. Oncology/Hematology,* 39:147-54). Late detection of the disease is common, and early pancreatic cancer diagnosis is rare in the clinical setting. This is significant, since late detection of pancreatic cancer results in low survival rate. Current treatment procedures available for pancreatic cancer have not led to a cure, or to a substantially improved survival time. Surgical resection has been the only modality that offers a chance at survival. However, due to a large tumor burden, only 10% to 25% of patients are candidates for "curative resection." For those patients undergoing a surgical treatment, the five-year survival rate is still poor, averaging only about 10%. A "non-endocrine pancreatic cancer" generally refers to cancers arising from the exocrine pancreatic glands. The term excludes pancreatic insulinomas and includes pancreatic carcinoma, pancreatic adenocarcinoma, adenosquamous carcinoma, squamous cell carcinoma and giant cell carcinoma and precursor lesions such as pancreatic intra-epithelial neoplasia (PanIN), mucinous cyst neoplasms (MCN) and intrapancreatic mucinous neoplasms (IPMN), which are neoplastic but not yet malignant. The terms "pancreatic cancer" and "non-endocrine pancreatic cancer" are used interchangeably herein.

In another embodiment, the cancer is colorectal cancer. Colon cancer is located in the large intestine, while rectal cancer is in the rectum. The difference between these two cancers is the location in the large intestine where the cancer occurs. Therefore, the term colorectal cancer is often used to refer to cancer in both locations. Colorectal cancer is third most common leading causes of cancer death in the United States. According to the "American Cancer Society Colorectal Cancer Facts and Figures. 2011-2013" (Atlanta, American Cancer Society, 2011), in 2001, the incidence rates of colorectal cancer per 100,000 are about 57.2 among male, and about 42.5 among female. In comparison, the mortality rates are 21.2 among male, and 14.9 among female per 100,000. As a whole, there will be about 141,000 new cases and 49,000 deaths in 2011. The common stages of colorectal cancer includes: Stage 0: when cancer is only on the innermost layer of the intestine; Stage I: when cancer is in the inner layer of the colon; Stage II: when cancer has spread through the muscle wall of the colon; Stage III: when cancer has spread to the lymph nodes; and Stage 1V: when cancer has spread to other organs. The most effective approach to treat colorectal cancer is early detection before symptoms develop by undergoing periodic colonoscopy or sigmoidoscopy when a person is 50 years or older, or has either a family history or personal history of colon cancer. The treatment options of colorectal cancer are surgery, radiation therapy and chemotherapy. 5-Fluorouracil, oxaliplatin and irinoteccan are commonly used chemotherapeutic agents for colorectal cancer.

As used herein, the term "cancer cell" is intended to include tumor cells, and refers to cells that divide at an abnormal (increased) rate. Cancer cells include, but are not limited to, carcinomas, such as squamous cell carcinoma, basal cell carcinoma, sweat gland carcinoma, sebaceous gland carcinoma, adenocarcinoma, papillary carcinoma, papillary adenocarcinoma, cystadenocarcinoma, medullary carcinoma, undifferentiated carcinoma, bronchogenic carcinoma, melanoma, renal cell carcinoma, hepatoma-liver cell carcinoma, bile duct carcinoma, cholangiocarcinoma, papillary carcinoma, transitional cell carcinoma, choriocarcinoma, semonoma, embryonal carcinoma, mammary carcinomas, gastrointestinal carcinoma, colonic carcinomas, bladder carcinoma, prostate carcinoma, and squamous cell carcinoma of the neck and head region; sarcomas, such as fibrosarcoma, myxosarcoma, liposarcoma, chondrosarcoma, osteogenic sarcoma, chordosarcoma, angiosarcoma, endotheliosarcoma, lymphangiosarcoma, synoviosarcoma and mesotheliosarcoma; leukemias and lymphomas such as granulocytic leukemia, monocytic leukemia, lymphocytic leukemia, malignant lymphoma, plasmocytoma, reticulum cell sarcoma, or Hodgkin's disease; and tumors of the nervous system including glioma, meningioma, medulloblastoma, schwannoma or epidymoma.

As used herein "contacting cancer cells" is defined as exposing the cancer cells to one or more combinations of agents described herein. In one embodiment, such combinations can be administered to cancer cells, directly or indirectly, using local, regional or systemic means.

As used herein a "cremophore" is a solvent that permits solubilization of a drug or compound. Various cremophores are well known to one of skill in the art, including but not limited to oil-based solvents.

As used herein "decreasing the size of a tumor" is defined as a reduction in the size of a tumor. Such an effect can be accomplished by reducing the number of proliferating tumor cells in the tumor (e.g., by reducing cell division of the tumor cells) and/or by inducing cytotoxicity or cell death (apoptosis) of existing tumor cells. Accordingly, tumor growth is arrested or prevented.

As used herein, the term "EGFR inhibitor" refers to an inhibitor of the epidermal growth factor receptor (EGFR). In one embodiment, the EGFR inhibitor is an antibody such as Erbitux™ (cetuximab, Imclone Systems Inc.) and ABX-EGF (panitumumab, Abgenix, Inc.). In another embodiment the EGFR inhibitor is a small molecule that competes with ATP such as Tarceva™ (erlotinib, OSI Pharmaceuticals), Iressa™ (gefitinib, Astra-Zeneca), tyrphostins described by Dvir et al. (1991) *JCB* 113:857-865; tricyclic pyrimidine compounds disclosed in U.S. Pat. No. 5,679,683; compound 6-(2,6-dichlorophenyl)-2-(4-(2-diethylaminoethoxy)phenylamino)-8-methyl-8H-pyrido(2,3-d)pyrimidin-7-one (known as PD166285) disclosed in Panek et al. (1997) *J. Pharm. Exp. Therap.* 283:1433-1444).

As used herein "increasing apoptosis" is defined as an increase in the rate of programmed cell death, i.e. more cells are induced into the death process as compared to exposure (contact with) either gemcitabine alone or the ceramide alone. Increasing apoptosis also includes the inhibition of cell division which results in a decrease in the total number of viable cancer cells.

As used herein, the term "inhibiting cancer" or "inhibiting cancer cell growth" is intended to include the inhibition of undesirable or inappropriate cell growth. The inhibition is intended to include inhibition of proliferation including rapid proliferation. The term "inhibiting cancer cell growth" is also intended to encompass inhibiting tumor growth which includes the prevention of the growth of a tumor in a subject or a reduction in the growth of a pre-existing tumor in a subject. The inhibition also can be the inhibition of the metastasis of a tumor from one site to another. A cancer is "inhibited" if at least one symptom of the cancer is alleviated, terminated, slowed, or prevented. As used herein, cancer is also "inhibited" if recurrence or metastasis of the cancer is reduced, slowed, delayed, or prevented.

The term "modulate" includes downregulation and upregulation. The term "downregulate," "decrease," "reduce," "inhibit," and the like are all used herein generally to mean a decrease by a statistically significant amount. The term "upregulate," "increase," "enhance," and the like are all used herein generally to mean an increase by a statistically significant amount. For example, an increase or a decrease can be by at least about 10%, 20%, 25%, 30%, 35%, 40%, 45%, 50%, 55%, 60%, 65%, 70%, 75%, 80%, 85%, 90%, 95%, 98%, 99%, 100%, 150%, 200%, 250%, 300%, 350%, 400%, 450%, 500%, 1000%, or more or any range in between 10-1000% inclusive as compared to a control. In some embodiments, the control can be a change in a cancer cell state such as cancer cell proliferation in the presence versus the absence of treatment. In another embodiment, the control can be activity of a wild type polypeptide of interest. An "overactivity" or "significantly higher level of activity" refers to an activity level of a molecule or test sample that is greater than the standard error of the assay employed to assess the activity, and is preferably at least twice, and more preferably three, four, five or ten or more times the activity relative to a reference or control sample and preferably, the average activity in several control samples. The term "underactivity" refers to the opposite of "overactivity."

A cancer cell is "resistant" to a therapeutic agent if its rate of growth is not inhibited, or inhibited to a very low degree, as a result of contact with the therapeutic agent when compared to its growth in the absence of contact with the therapeutic agent. The quality of being resistant to a therapeutic agent is a highly variable one, with different cancer cells exhibiting different levels of "resistance" to a given therapeutic agent under different conditions.

A cancer cell is "sensitive" to a therapeutic agent if its rate of growth is inhibited as a result of contact with a therapeutic agent, compared to its growth in the absence of contact with the therapeutic agent. The quality of being sensitive to a therapeutic agent is a variable one, with different cancer cells exhibiting different levels of "sensitivity" to a given therapeutic agent, under different conditions.

Determination of whether a patient is "sensitive" or "resistant" to a therapeutic agent and/or protocol can be readily made by the physician (the "attending clinician"), as one skilled in the art, by the use of known techniques. For example, a number of factors are considered by the attending clinician, including, but not limited to: the specific cancer involved; pharmacodynamic characteristics of the particular therapeutic agent; the size, age, and general health of the patient; the degree of or involvement or the severity of the cancer; the particular compound administered; the mode of administration; and other relevant circumstances.

As used herein, the term "survival" includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g., time of diagnosis or start of treatment) and end point (e.g., death, recurrence or metastasis). In addition, criteria for efficacy of treatment can be expanded to include response to chemotherapy, probability of survival, probability of metastasis within a given time period, and probability of tumor recurrence.

As used herein, the term "subject" shall mean any animal including, without limitation, a human, a mouse, a rat, a rabbit, a non-human primate, or any other mammal. In one embodiment, the subject is a primate. In another embodiment, the subject is a human.

As used herein, the term "synergistic" refers to a combination of therapeutic agents described herein, which, when taken together, is more effective than the additive effects of the individual therapies. A synergistic effect of a combination of therapies (e.g., a combination of therapeutic agents) permits the use of lower dosages of one or more of the therapeutic agent(s) and/or less frequent administration of the agent(s) to a subject with a disease or disorder, e.g., a proliferative disorder. The ability to utilize lower the dosage of one or more therapeutic agent and/or to administer the therapeutic agent less frequently reduces the toxicity associated with the administration of the agent to a subject without reducing the efficacy of the therapy in the treatment of a disease or disorder. In addition, a synergistic effect can result in improved efficacy of agents in the prevention, management or treatment of a disease or disorder, e.g. a proliferative disorder. Finally, a synergistic effect of a combination of therapies may avoid or reduce adverse or unwanted side effects associated with the use of either therapeutic agent alone. As used herein, the term "in combination" refers to the use of more than one therapeutic agent. The use of the term "in combination" does not restrict the order in which the therapeutic agents are administered to a subject with a disease or disorder, e.g., a proliferative disorder. A first therapeutic agent, such as a compound described herein, can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent, such as an anti-cancer agent, to a subject with a disease or disorder, e.g. a proliferative disorder, such as cancer.

A "transcribed polynucleotide" or "nucleotide transcript" is a polynucleotide (e.g. an mRNA, hnRNA, a cDNA, or an analog of such RNA or cDNA) which is complementary to or homologous with all or a portion of a mature mRNA made by transcription of a marker of the invention and normal post-transcriptional processing (e.g. splicing), if any, of the RNA transcript, and reverse transcription of the RNA transcript.

There is a known and definite correspondence between the amino acid sequence of a particular protein and the nucleotide sequences that can code for the protein, as defined by the genetic code (shown below). Likewise, there is a known and definite correspondence between the nucleotide sequence of a particular nucleic acid and the amino acid sequence encoded by that nucleic acid, as defined by the genetic code.

| GENETIC CODE | |
|---|---|
| Alanine (Ala, A) | GCA, GCC, GCG, GCT |
| Arginine (Arg, R) | AGA, ACG, CGA, CGC, CGG, CGT |
| Asparagine (Asn, N) | AAC, AAT |
| Aspartic acid (Asp, D) | GAC, GAT |
| Cysteine (Cys, C) | TGC, TGT |
| Glutamic acid (Glu, E) | GAA, GAG |
| Glutamine (Gln, Q) | CAA, CAG |
| Glycine (Gly, G) | GGA, GGC, GGG, GGT |
| Histidine (His, H) | CAC, CAT |
| Isoleucine (Ile, I) | ATA, ATC, ATT |
| Leucine (Leu, L) | CTA, CTC, CTG, CTT, TTA, TTG |
| Lysine (Lys, K) | AAA, AAG |
| Methionine (Met, M) | ATG |
| Phenylalanine (Phe, F) | TTC, TTT |
| Proline (Pro, P) | CCA, CCC, CCG, CCT |
| Serine (Ser, S) | AGC, AGT, TCA, TCC, TCG, TCT |
| Threonine (Thr, T) | ACA, ACC, ACG, ACT |
| Tryptophan (Trp, W) | TGG |
| Tyrosine (Tyr, Y) | TAC, TAT |
| Valine (Val, V) | GTA, GTC, GTG, GTT |
| Termination signal (end) | TAA, TAG, TGA |

An important and well known feature of the genetic code is its redundancy, whereby, for most of the amino acids used to make proteins, more than one coding nucleotide triplet may be employed (illustrated above). Therefore, a number of different nucleotide sequences may code for a given amino acid sequence. Such nucleotide sequences are considered functionally equivalent since they result in the production of the same amino acid sequence in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid.

In view of the foregoing, the nucleotide sequence of a DNA or RNA coding for a fusion protein or polypeptide of the invention (or any portion thereof) can be used to derive the fusion protein or polypeptide amino acid sequence, using the genetic code to translate the DNA or RNA into an amino acid sequence. Likewise, for fusion protein or polypeptide amino acid sequence, corresponding nucleotide sequences that can encode the fusion protein or polypeptide can be deduced from the genetic code (which, because of its redundancy, will produce multiple nucleic acid sequences for any given amino acid sequence). Thus, description and/or disclosure herein of a nucleotide sequence which encodes a fusion protein or polypeptide should be considered to also include description and/or disclosure of the amino acid sequence encoded by the nucleotide sequence. Similarly, description and/or disclosure of a fusion protein or polypeptide amino acid sequence herein should be considered to also include description and/or disclosure of all possible nucleotide sequences that can encode the amino acid sequence.

II. Therapeutic Agents and Pharmaceutical Compositions

The methods of the present invention use combinations of therapeutic agents in a pharmaceutical composition as described below.

A. Ceramide

The term "ceramide" generally refers to any N-acylsphingosine. Ceramides include sphingolipids in which the sphingosine is acylated with a fatty acid acyl CoA derivative to form an N-acylsphingosine. Ceramide may be either naturally occurring or chemically synthesized. Preferably, the carbon chain length is less than 18 carbons. Examples include C6-ceramide (N-hexanoyl-D-sphingosine), C2-ceramide (N-acetyl-D-sphingosine), C8-ceramide (N-octyl-D-sphingosine) and C16-ceramide (N-palmitoyl-D-sphingosine). Other ceramides are known to persons having ordinary skill in the art. In certain embodiments of the above-described methods and composition, the ceramide may be a C2-ceramide, C6-ceramide, C8-ceramide, C16-ceramide, or a higher order of ceramide. In one embodiment, the ceramide is C6-ceramide. For each embodiment of the present invention described herein relating to C6-ceramide, each of the other orders of ceramide known to the skilled artisan are also contemplated mutatis mutandis. Ceramide, which is normally lipid soluble, can be made water soluble according to well-known methods in order to enable contact with cancer cells (e.g., in a subject). Ceramide may be solubilized initially in alcohol and then subsequently diluted in saline or a cremophore.

The amount of ceramide is from about 1.0 mg/kg-about 10.0 mg/kg every two weeks. In a further embodiment, the amount of ceramide is about 10.0 mg/kg every two weeks. In a further embodiment, the amount of ceramide is about 2.0 mg/kg, 3.0 mg/kg, 4.0 mg/kg, 5.0 mg/kg, 6.0 mg/kg, 7.0 mg/kg, 8.0 mg/kg, 9.0 mg/kg, 10.0 mg/kg, 11.0 mg/kg, 12.0 mg/kg, 13.0 mg/kg, 14.0 mg/kg or 15.0 mg/kg every two weeks.

For each embodiment described herein, the ratio of ceramide to other therapeutic agent composition of a therapeutic combination described herein can be 1:1, 1.5:1, 2:1, 2.5:1, 3:1, 3.5:1, 4:1, 4.5:1, 5:1, 5.5:1, 6:1, 6.5:1, 7:1, 7.5:1 or greater or any range in between.

B. Therapeutic Agents

As used herein, the term "anti-cancer agent" and "therapeutic agent" is defined broadly as anything that cancer cells, including tumor cells, may be exposed to in a therapeutic protocol for the purpose of inhibiting their growth or kill the cells. In one embodiments, such agents can be used according to the methods described herein either in conjunction with ceramide (e.g., C6-ceramide), in conjunction with each other (e.g., LY294002 plus gemcitabine, taxol plus U0126, taxol plus gemcitabine, etc.), or in any combination thereof. In the context of the present invention, such agents include, but are not limited to, chemotherapeutic agents, such as anti-metabolic agents, e.g., Ara AC, 5-FU and methotrexate, antimitotic agents, e.g., TAXOL, inblastine and vincristine, alkylating agents, e.g., melphalan, BCNU and nitrogen mustard, topoisomerase II inhibitors, e.g., VW-26, topotecan and Bleomycin, strand-breaking agents, e.g., doxorubicin and DHAD, cross-linking agents, e.g., cisplatin and CBDCA, radiation and ultraviolet light.

As used herein, the term "chemotherapeutic agent" is intended to include chemical reagents which inhibit the growth of proliferating cells or tissues wherein the growth of such cells or tissues is undesirable. Particular chemotherapeutic agents include, but are not limited to (i) antimetabolites, such as cytarabine, fludarabine, 5-fluoro-2'-deoxyuiridine, gemcitabine, hydroxyurea or methotrexate; (ii) DNA-fragmenting agents, such as bleomycin, (iii) DNA-crosslinking agents, such as chlorambucil, cisplatin, cyclophosphamide or nitrogen mustard; (iv) intercalating agents such as adriamycin (doxorubicin) or mitoxantrone; (v) protein synthesis inhibitors, such as L-asparaginase, cycloheximide, puromycin or diphtheria toxin; (Vi) topoisomerase I poisons, such as camptothecin or topotecan; (vii) topoisomerase II poisons, such as etoposide (VP-16) or teniposide; (viii) microtubule-directed agents, such as colcemid, colchicine, paclitaxel, vinblastine or vincristine; (ix) kinase inhibitors such as flavopiridol, staurosporin, STI571 (CPG 57148B) or UCN-01 (7-hydroxystaurosporine); (x) enhancers of the AMPK signaling pathway, (xi) inhibitors of the PI3K/AKT/mTORC1 signaling pathway, (xii) inhibitors of the MEK/ERK signaling pathway, (xiii) miscellaneous investigational agents such as thioplatin, PS-341, phenylbutyrate, ET-18-OCH3, or farnesyl transferase inhibitors (L-739749, L-744832); polyphenols such as quercetin, resveratrol, piceatannol, epigallocatechine gallate, theaflavins, flavanols, procyanidins, betulinic acid and derivatives thereof; (xiV) hormones such as glucocorticoids or fenretinide; and (xv) hormone antagonists, such as tamoxifen, finasteride or LHRH antagonists. In an embodiment, the chemotherapeutic compound is one or more of gemcitabine, cisplatin, doxorubicin, daunarubicin, paclitaxel, taxotere and mitomycin C. In a particular embodiment, the chemotherapeutic compound is one or more of gemcitabine, cisplatin and paclitaxel.

Chemotherapeutic agents are well known in the art (see e.g., Gilman A. G., et al., *The Pharmacological Basis of Therapeutics*, 8th Ed., Sec 12:1202-1263 (1990)), and are typically used to treat neoplastic diseases. The chemotherapeutic agents generally employed in chemotherapy treatments are listed below in Table 1.

TABLE 1

| CLASS | TYPE OF AGENT | NONPROPRIETARY NAMES (OTHER NAMES) |
|---|---|---|
| Alkylating | Nitrogen Mustards | Mechlorethamine ($HN_2$) |
|  |  | Cyclophosphamide |
|  |  | Ifosfamide |
|  |  | Melphalan (L-sarcolysin) |
|  |  | Chlorambucil |
|  | Ethylenimines And Methylmelamines | Hexamethylmelamine Thiotepa |
|  | Alkyl Sulfonates | Busulfan |
| Alkylating | Nitrosoureas | Carmustine (BCNU) |
|  |  | Lomustine (CCNU) |
|  |  | Semustine (methyl-CCNU) |
|  |  | Streptozocin (streptozotocin) |
|  | Triazenes | Decarbazine (DTIC; imethyltriazenoimidazolecarboxamide) |
|  | Alkylator | cis-diamminedichloroplatinum II (CDDP) |
| Antimetabolites | Folic Acid Analogs | Methotrexate (amethopterin) |
|  | Pyrimidine Analogs | Fluorouracil ('5-fluorouracil; 5-FU) |
|  |  | Floxuridine (fluorode-oxyuridine; FUdR) |
|  |  | Cytarabine (cytosine arabinoside) |
|  |  | gemcitabine (deoxycytidine analog) |
|  | Purine Analogs and Related Inhibitors | Mercaptopuine (6-mercaptopurine; 6-MP) Thioguanine (6-thioguanine; TG) Pentostatin (2'-deoxycoformycin) |

TABLE 1-continued

| CLASS | TYPE OF AGENT | NONPROPRIETARY NAMES (OTHER NAMES) |
|---|---|---|
| Natural Products | Vinca Alkaloids | Vinblastin (VLB) Vincristine |
| | Topoisomerase Inhibitors | Etoposide Teniposide Camptothecin Topotecan 9-amino-campotothecin CPT-11 |
| | Antibiotics | Dactinomycin (actinomycin D) Adriamycin (Doxorubicin) Daunorubicin (daunomycin; rubindomycin) Doxorubicin Bleomycin Plicamycin (mithramycin) Mitomycin (mitomycin C) TAXOL (paclitaxel) Taxotere |
| | Enzymes | L-Asparaginase |
| | Biological Response Modifiers | Interfon alfa interleukin 2 |
| Misc. Agents | Platinum Coordination Complexes | cis-diamminedichloroplatinum II (CDDP) Carboplatin Oxaliplatin Cisplatin |
| | Anthracendione | Mitoxantrone |
| | Substituted Urea | Hydroxyurea |
| | Methyl Hydraxzine Derivative | Procarbazine (N-methylhydrazine, (MIH) |
| | Adrenocortical Suppressant | Mitotane (o,p'-DDD) Aminoglutethimide |
| Hormones and Antagonists | Adrenocorticosteroids | Prednisone Dexamethasone |
| | Progestins | Hydroxyprogesterone Caproate Medroxyprogesterone Acetate Megestrol acetate |
| | Estrogens | Diethylstilbestrol Ethinyl estradiol |
| | Antiestrogen | Tamoxifen |
| | Androgens | Testosterone propionate Fluoxymesterone |
| | Antiandrogen | Flutamide |
| | Gonadotropin-releasing Hormone analog | Leuprolide |

The chemotherapeutic agents used in the present methods can be a single agent or a combination of agents. Preferred combinations will include agents that have different mechanisms of action, e.g., the use of an anti-mitotic agent in combination with an alkylating agent.

As used herein, the term "pro-survival" or "pro-growth" pathways refer to signaling pathways used by cancer cells to promote their growth and/or survival. The term "pathway" is intended to mean a set of system components involved in two or more sequential molecular interactions that result in the production of a product or activity. A pathway can produce a variety of products or activities that can include, for example, intermolecular interactions, changes in expression of a nucleic acid or polypeptide, the formation or dissociation of a complex between two or more molecules, accumulation or destruction of a metabolic product, activation or deactivation of an enzyme or binding activity. Thus, the term "pathway" includes a variety of pathway types, such as, for example, a biochemical pathway, a gene expression pathway, and a regulatory pathway. Similarly, a pathway can include a combination of these exemplary pathway types. Intracellular signaling via several pathways, such as AMPK, PI3K/AKT, MEK/ERK, and JAK/STAT signaling pathways, leading to the activation of anti-apoptotic proteins and the inactivation of pro-apoptotic proteins (reviewed in Henson and Gibson, 2006, Cellular Signaling 18:2089-2097). Without being bound by theory, it is believed that ceramide increases apoptosis in cancer cells and such desired cancer cell death is antagonized by pro-survival pathways. Accordingly, therapeutic agents that inhibit such pro-survival pathways are contemplated as useful therapeutic agents in combination with ceramide.

In one embodiment, the pro-survival pathway is the AMP-activated protein kinase (AMPK) signaling pathway. AMPK has a role in regulating the mTOR pathway. Mammalian target of rapamycin (mTOR) is a serine/threonine kinase and a key regulator of protein synthesis. To inhibit cell growth and protect cells from apoptosis induced by glucose starvation, AMPK phosphorylates TSC2 at Thr-1227 and Ser-1345 increasing the activity of the TSC1 and TSC-2 complex to inhibit m-TOR. In addition, AMPK inhibits mTOR action by phosphorylation on Thr-2446. Thus, AMPK indirectly and directly inhibits the activity of mTOR to limit protein synthesis. AMPK may also be a therapeutic target for many cancers that have constitutive activation of the PI3K-Akt signaling pathway. Treatment of various cancer cell lines by AICAR attenuated the cell proliferation both in-vitro and in-vivo studies (Rattan et al., JBC 280, 39582 (2005)). Reports link the treatment of metformin with a lower risk of cancer in diabetic patients (Evans et al., BMJ 330, 1304 (2005)). The activation of AMPK by AICAR has been shown to reduce expression of the lipogenic enzymes FAS and ACC, resulting in suppression of proliferation in prostate cancer cells. Many cancer cells display a markedly increased rate of de novo fatty acid synthesis correlated with high levels of FAS. Inhibition of FAS suppresses cancer cell proliferation and induces cell death. Thus, AMPK activation and inhibition of FAS activity is a clear target for pharmacological therapy of cancers.

In another embodiment, the pro-survival pathway is the PI3K/AKT/mTORC1 signaling pathway. The "PI3K/AKT signaling pathway" or "AKT signaling pathway" refers to one of the intracellular signaling pathways activated by the binding of growth factors to receptor tyrosine kinases. On activation, PI3K phosphorylates phosphatidylinositol-4,5-bisphosphate (PIP2) to phosphatidylinositol-3,4,5-triphosphate (PIP3), a process that is reversed by PTEN. PIP3 signals activate the kinase PDK1, which in turn activates the kinase AKT. The AKT protein family, which members are also called protein kinases B (PKB) plays an important role in mammalian cellular signaling. Akt kinase is a serine/threonine kinase which is a downstream effector molecule of phosphoinositide 3-kinase and is involved in protecting a cell from apoptosis. Akt kinase is thought to be involved in the progression of cancer because it stimulates cell proliferation and suppresses apoptosis. Akt1 is involved in cellular survival pathways, by inhibiting apoptotic processes. Akt1 is also able to induce protein synthesis pathways, and is therefore a key signaling protein in the cellular pathways that lead to skeletal muscle hypertrophy, and general tissue growth. Since it can block apoptosis, and thereby promote cell survival, Akt1 has been implicated as a major factor in many types of cancer. Akt is known to play a role in the cell cycle. Under various circumstances, activation of Akt was shown to overcome cell cycle arrest in G1 and G2 phases. Moreover, activated Akt may enable proliferation and survival of cells that have sustained a potentially mutagenic impact and, therefore, may contribute to acquisition of mutations in other genes. AKT (activation, amplification) and PTEN (mutation, deletion, epigenetic inactivation) are deregulated in many human cancers (Altomare et al., 2003, J. Cell Biochem. 88:470-476; Ruggeri et al., 1998, Mol. Carcinog. 21:81-86; Cheng et al., 1996, Proc. Natl. Acad. Sci. USA 93:3636-3641; Staal et al., 1987, Proc. Natl. Acad. Sci. USA 84:5034-5037; Li et al., 2005, World J. Gastroenterol. 11:285-288; Li et al., 1997, Science 275:1943-1947; Goel et al., 2004, 64:3014-3021). PI3K pathway activation can be assessed by immunohistochemical analysis of PTEN or phosphorylated AKT levels in clinical samples (Slipicevic et al., 2005, Am. J. Clin. Pathol. 124:528-536). Molecular targets of such inhibitors include, but are not limited to, PI3K, AKT, mTORC1, mTORC2, PDK1, MYC, cMET, FGFR2, growth factors (EGF, b-FGF, IGF1, Insulin, or Heregulin) and the like. Other molecular targets are well known in the art and are described, for example, in US 2011-0015869.

Exemplary inhibitors of PI3K/AKT signaling are also well known in the art and include, but are not limited to: phosphatidylinositol ether lipid analogs, alkylphospholipid analogs, allosteric AKT inhibitors, HSP90 inhibitor, alkylphospholipid perifosine, rapamycin, RAD001, FTY720, PDK1 inhibitors (BX-795, BX-912, and BX-320 (Feldman et al., 2005, J. Biol. Chem. 280:19867-19874); 7-hydroxystaurosporine (Sato et al., 2002, Oncogene, 21:1727-1738)); PI3K inhibitors (wortmannin (Wymann et al., 1996, Mol. Cell. Biol. 16:1722-1733); LY294002 (Vlahos et al., 1994, J. Biol. Chem. 269:5241-5248; Wetzker and Rommel, 2004, Curr. Pharm. Des. 10:1915-1922); IC87114 (Finan and Thomas, 2004, Biochem. Soc. Trans. 32:378-382; WO0181346); WO01372557; U.S. Pat. No. 6,403,588; WO0143266); AKT antibodies (Shin et al., 2005, Cancer Res. 65:2815-2824) (see also Cheng et al., Oncogene, 2005, 24:7482-7492 for review on inhibitors of AKT pathway), and IGF1R inhibitors (such as monoclonal antibody MK-0646 U.S. Pat. No. 7,241,444). The inhibitors and agents listed in the Examples section that were used to identify and refine the growth factor signaling pathway biomarkers are also exemplary growth factor pathway agents (i.e., AKT1/2 inhibitors L-001154547 ('547; 3-phenyl-2-(4-{[4-(5-pyridin-2-yl-1H-1,2,4-triazol-3-yl)piperidin-1-yl]me-thyl}phenyl)-1,6-naphthyridin-5(6H)-one; disclosed in WO2006065601), L-01173931 ('931; 6-Methyl-3-phenyl-2-(4-{[4-(5-pyridin-2-yl-1H-1,2,4-triazol-3-yl) piperidi-n-1-yl]-methyl}phenyl)-1,6-naphthyridin-5(6H)-one; disclosed in WO2006065601; gamma secretase inhibitor 421B (U.S. Pat. No. 7,138,400 and WO02/36555); cMET inhibitors L-001501404 (4-(6-Phenyl-[1,2,4]triazolo [4,3-b][1,2,4]triazin-3-ylmethyl)-phenol, see also U.S. Pat. No. 7,122,548), MK-2461 (N-[(2R)-1,4-dioxan-2-ylmethyl]-N-methyl-N'-[3-(1-methyl-1H-pyrazol-4-yl)-5-oxo-5H-benzo[4,5]cyclohepta[1,2-b]pyridin-7-yl]sulfamide), and L-001793225 (1-[3-(1-Methyl-1H-pyrazol-4-yl)-5-oxo-5H-benzo[4,5]cyclohepta[1,2-b]pyri-din-7-yl]-N-(pyridin-2-ylmethyl)methanesulfonamide.

In still another embodiment, the pro-survival pathway is the MEK/ERK signaling pathway. The extracellular signal-regulated kinases (ERKs) are activated by multiple signals including growth factors, cytokines, transforming growth factors, and G protein-coupled receptors. These signals lead to activation of RAS small G proteins which activate RAF kinases. Active RAF kinases phosphorylate and activate MEK kinases, which subsequently phosphorylate and activate ERK1/2 kinases. ERK1/2 kinases phosphorylate and regulate numerous substrates including other protein kinases, protein phosphatases, transcription factors, scaffolding proteins, signaling molecules and apoptosis-related proteins which lead to a variety of cell type and context-dependent responses. Constitutive activation of ERK1/2 by activating mutations in NRAS or BRAF is observed in the majority of melanomas and plays an integral role in the regulation of proliferation, invasiveness, and survival. In one embodiment, "ERK signaling" is signaling involving or mediated by the kinase activity of ERK1/2 kinases. In another embodiment, ERK signaling comprises signal transduction via downstream targets of ERK1/2 kinase activity. Components of the ERK signaling pathway are known to those of ordinary skill in the art. For example, in humans, components of the ERK signaling pathway that can positively regulate ERK signaling include, for example, BRAF (NCBI Gene ID No: 673); EGFR (NCBI Gene ID No: 1956); HER2 (NCBI Gene ID No: 2064); c-KIT (NCBI Gene ID No: 3815); MET (NCBI Gene ID No: 4233); MEK1 (NCBI Gene ID No: 5604); MEK2 (NCBI Gene ID No: 5605); ERK1 (NCBI Gene ID No: 5595); ERK2 (NCBI Gene ID No: 5594); HRAS (NCBI Gene ID No: 3265); KRAS (NCBI Gene ID No: 3845); and NRAS (NCBI Gene ID No: 4893).

An inhibitor of ERK signaling can be an antagonist of any component of the ERK signaling pathway that positively regulates ERK signaling, e.g. BRAF or MEK, or an agent which decreases the amount or activity of those components, e.g. an RNAi molecule. An inhibitor of ERK signaling can be an agonist of any component of the ERK signaling pathway which negatively regulates ERK signaling, or an agent which increases the amount or activity of those components. In some embodiments, an inhibitor of ERK signaling specifically inhibits the kinase activity of one or more RAF kinases or an ortholog thereof, e.g., it decreases the phosphorylation of one or more MEK kinases. In some embodiments, an inhibitor of ERK signaling is a specific inhibitor of the activity of BRAF. In some embodiments, an inhibitor of ERK signaling is a specific inhibitor of the activity of a mutant form of BRAF. In some embodiments, an inhibitor of ERK signaling is a specific inhibitor of the activity of BRAF.sup.V600E. In some embodiments, an inhibitor of ERK signaling specifically inhibits the kinase activity of one or more MEK kinase or an ortholog thereof, e.g., it decreases the phosphorylation of ERK1/2. In some embodiments, an inhibitor of ERK signaling specifically inhibits the kinase activity of one or more of ERK1 and ERK2 kinases or an ortholog thereof, e.g., it decreases the phosphorylation of a substrate of ERK1/2. Inhibition of ERK signaling can be measured according to methods well-known to those of ordinary skill in the art. By way of non-limiting example, inhibition of ERK signaling can be measured by determining the level of dual-phosphorylated ERK1/2 (ppERK1/2) as described in detail elsewhere herein. In brief, the level of ppERK1/2 can be detected by immunoblot assay. Contacting a cell with an agent that is an inhibitor of ERK signaling will cause the cell to exhibit a lower level of ppERK1/2 than a cell not contacted with the agent. Components of the ERK signaling pathway that can negatively regulate ERK signaling include, for example, SGK1 (NCBI Gene ID No: 6446); IGFBP7 (NCBI Gene ID No: 3490); SPRED1 (NCBI Gene ID No: 161742); and KSR1 (NCBI Gene ID No: 8844).

In some embodiments, the inhibitor of ERK signaling can be an inhibitor of MEK. As used herein, the term "inhibitor of MEK" refers to a compound or agent, such as a small molecule, that inhibits, decreases, lowers, or reduces the activity of MEK. Examples of inhibitors of MEK include, but are not limited to, AZD6244 (6-(4-Bromo-2-chloro-phenylamino)-7-fluoro-3-methyl-3H-benzoimida-zole-5-carboxylic acid (2-hydroxy-ethoxy)-amide; selumetinib; Structure IV), and U0126 (1,4-diamino-2,3-dicyano-1,4-bis [2-aminophenylthio]butadiene; ARRY-142886; Structure V). Further non-limiting examples of MEK inhibitors include PD0325901, AZD2171, GDC-0973/XL-518, PD98059, PD184352, GSK1120212, RDEA436, RDEA119/BAY869766, AS703026, BIX 02188, BIX 02189, CI-1040 (PD184352), PD0325901, and PD98059. These and other inhibitors of MEK, as well as non-limiting examples of their methods of manufacture, are described in U.S. Pat. Nos. 5,525,625; 6,251,943; 7,820,664; 6,809,106; 7,759,518; 7,485,643; 7,576,072; 7,923,456; 7,732,616; 7,271,178; 7,429,667; 6,649,640; 6,495,582; 7,001,905; US Patent Publication No. US2010/0331334, US2009/0143389, US2008/0280957, US2007/0049591, US2011/0118298, International Patent Application Publication No. WO98/43960, WO99/01421, WO99/01426, WO00/41505, WO00/42002, WO00/42003, WO00/41994, WO00/42022, WO00/42029, WO00/68201, WO01/68619, WO02/06213 and WO03/077914, the contents of which are herein incorporated by reference in their entireties.

In another embodiment, a therapeutic agent is an inhibitor of EGFR. Epidermal Growth Factor Receptor (EGFR) is a member of the type 1 subgroup of receptor tyrosine kinase family of growth factor receptors which play critical roles in cellular growth, differentiation and survival. Activation of these receptors typically occurs via specific ligand binding which results in hetero- or homodimerization between receptor family members, with subsequent autophosphorylation of the tyrosine kinase domain. Specific ligands which bind to EGFR include epidermal growth factor (EGF), transforming growth factor alpha (TGF alpha), amphiregulin and some viral growth factors. Activation of EGFR triggers a cascade of intracellular signaling pathways involved in both cellular proliferation (the ras/raf/MAP kinase pathway) and survival (the PI3 kinase/Akt pathway). Members of this family, including EGFR and HER2, have been directly implicated in cellular transformation. A number of human malignancies are associated with aberrant or overexpression of EGFR and/or overexpression of its specific ligands. Gullick, Br. Med. Bull. (1991), 47:87-98; Modijtahedi & Dean, Int. J. Oncol. (1994), 4:277-96; Salomon, et al., Crit. Rev. Oncol. Hematol. (1995), 19:183-232. Aberrant or over-expression of EGFR has been associated with an adverse prognosis in a number of human cancers, including head and neck, breast, colon, prostate, lung (e.g., NSCLC, adenocarcinoma and squamous lung cancer), ovarian, gastrointestinal cancers (gastric, colon, pancreatic), renal cell cancer, bladder cancer, glioma, gynecological carcinomas and prostate cancer. In some instances, overexpression of tumor EGFR has been correlated with both chemoresistance and a poor prognosis. Lei, et al., Anti-cancer Res. (1999), 19:221-28; Veale, et al., Br. J. Cancer (1993); 68:162-65. Mutations in EGFR are associated with many types of cancer as well. For example, EGFR mutations are highly prevalent in non-mucinous BAC patients. Finberg, et al., J. Mol. Diagnostics. (2007) 9(3):320-26. In an embodiment the EGFR inhibitor is an antibody such as Erbitutux™ (cetuximab, Imclone Systems Inc.) and ABX-EGF (panitumumab, Abgenix, Inc.). In another embodiment the EGFR inhibitor is a small molecule that competes with ATP such as Tarceva™ (erlotinib, OSI Pharmaceuticals), Iressa™ (gefitinib, Astra-Zeneca), tyrphostins described by Dvir, et al., J. Cell Biol., 113:857-865 (1991); tricyclic pyrimidine compounds disclosed in U.S. Pat. No. 5,679,683; compound 6-(2,6-dichlorophenyl)-2-(4-(2-diethylaminoethoxy)phenylamino)-8-methyl-8H-pyrido(2,3-d)pyrimidin-7-one (known as PD166285) disclosed in Panek, et al., Journal of Pharmacology and Experimental Therapeutics 283, 1433-1444 (1997).

In addition to the specific agents described above, it is further contemplated that a polypeptide, an antibody or antigen binding fragment thereof, a toxin, an RNA interfering molecule, an siRNA molecule, and shRNA molecule, an antisense oligonucleotide, a peptide, a peptidomimetic, an aptamer, and the like, as well as combinations thereof, that appropriately enhance or inhibit the targets of pro-survival signaling pathways can also be used as a therapeutic agent according to the present invention. In particular, the nucleic acid sequence, amino acid sequence, functional domain, structural domain, gene locus, and other identifying information for the signaling pathway targets described herein are well known in the art. For example, KRAS nucleic acid and amino acid sequences from many organisms is well known in the art and include, for example, canine KRAS (NCBI Accession XM_540523.3, XP_540523.3, XM_003432429.1, and XP_00343247.1), chimpanzee KRAS (NCBI Accession XM_003313794.1, XP_003313842.1, XM_528758.3, and XP_528758.3), cow KRAS (NCBI Accession NM_001110001.1 and NP_001103471.1), mouse KRAS (NCBI Accession NM_021284.6 and NP_067259.4), rat KRAS (NCBI Accession NM_031515.3 and NP_113703.1), chicken KRAS (NCBI Accession NM_001256162.1 and NP_001243091.1), and zebrafish KRAS (NCBI Accession NM_001003744.1 and NP_001003744.1). Human KRAS sequences include the following:

amino acid residues that are not essential for activity. Such polypeptides differ in amino acid sequence from the naturally-occurring proteins, yet retain biological activity. In one embodiment, such a protein has an amino acid sequence that is at least about 40% identical, 50%, 60%, 70%, 75%, 80%, 83%, 85%, 87.5%, 90%, 91%, 92%, 93%, 94%, 95%, 96%, 97%, 98%, 99% or identical to the amino acid sequence of one of the target proteins. An isolated nucleic acid molecule encoding a variant protein can be created by introducing one

```
KRAS isoform a coding nucleic acid sequence (NCBI Accession NM_033360.2):
  1  atgactgaat ataaacttgt ggtagttgga gctggtggcg taggcaagag tgccttgacg 61  atacagctaa ttcagaatca ttttgtggac gaatatgatc caacaataga ggattcctac 121  aggaagcaag tagtaattga tggagaaacc tgtctcttgg atattctcga cacagcaggt 181  caagaggagt acagtgcaat gagggaccag tacatgagga ctggggaggg ctttctttgt 241  gtatttgcca taaataatac taaatcattt gaagatattc accattatag agaacaaatt 301  aaaagagtta aggactctga agatgtacct atggtcctag taggaaataa atgtgatttg 361  ccttctagaa cagtagacac aaaacaggct caggacttag caagaagtta tggaattcct 421  tttattgaaa catcagcaaa gacaagacag agagtggagg atgcttttta tacattggtg 481  agggagatcc gacaatacag attgaaaaaa atcagcaaag aagaaagac tcctggctgt 541  gtgaaaatta aaaaatgcat tataatgtaa
```

```
KRAS isoform an amino acid sequence (NCBI Accession NP_203524.1):
  1  mteyklvvvg aggvgksalt iqliqnhfvd eydptiedsy rkqvvidget clldildtag 61  qeeysamrdq ymrtgegflc vfainntksf edihhyreqi krvkdsedvp mvlvgnkcdl 121  psrtvdtkqa qdlarsygip fietsaktrq rvedafytlv reirqyrlkk iskeektpgc 181  vkikkciim
```

```
KRAS isoform b coding nucleic acid sequence (NCBI Accession NM_004985.3):
  1  atgactgaat ataaacttgt ggtagttgga gctggtggcg taggcaagag tgccttgacg 61  atacagctaa ttcagaatca ttttgtggac gaatatgatc caacaataga ggattcctac 121  aggaagcaag tagtaattga tggagaaacc tgtctcttgg atattctcga cacagcaggt 181  caagaggagt acagtgcaat gagggaccag tacatgagga ctggggaggg ctttctttgt 241  gtatttgcca taaataatac taaatcattt gaagatattc accattatag agaacaaatt 301  aaaagagtta aggactctga agatgtacct atggtcctag taggaaataa atgtgatttg 361  ccttctagaa cagtagacac aaaacaggct caggacttag caagaagtta tggaattcct 421  tttattgaaa catcagcaaa gacaagacag ggtgttgatg atgccttcta tacattagtt 481  cgagaaattc gaaaacataa agaaaagatg agcaaagatg gtaaaaagaa gaaaaagaag 541  tcaaagacaa agtgtgtaat tatgtaa
```

```
KRAS isoform b amino acid sequence (NCBI Accession NP_004976.2):
  1  mteyklvvvg aggvgksalt iqliqnhfvd eydptiedsy rkqvvidget clldildtag 61  qeeysamrdq ymrtgegflc vfainntksf edihhyreqi krvkdsedvp mvlvgnkcdl 121  psrtvdtkqa qdlarsygip fietsaktrq gvddafytlv reirkhkekm skdgkkkkkk 181  sktkcvim
```

The present invention further provides variants, fragments, and functionally similar homologs of the pro-survival signaling pathway targets for enhanced or inhibited activity according to the methods described further herein. For example, a nucleic acid molecule of such a target can comprise only a portion of a nucleic acid sequence needed to alter target activity. For example, such nucleic acid molecules can encode a polypeptide that contains changes in or more nucleotide substitutions, additions or deletions into the nucleotide sequence of nucleic acids of the invention, such that one or more amino acid residue substitutions, additions, or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art.

In some embodiments, antisense nucleic acid molecules, i.e., molecules which are complementary to a sense nucleic acid target, e.g., complementary to the coding strand of a double-stranded cDNA or mRNA molecule, is useful. Accordingly, an antisense nucleic acid molecule can hydrogen bond to (i.e. anneal with) a sense nucleic acid target. The antisense nucleic acid can be complementary to an entire coding strand, or to only a portion thereof, e.g., all or part of the protein coding region (or open reading frame). An antisense nucleic acid molecule can also be antisense to all or part of a non-coding region of the coding strand of a nucleotide sequence encoding a polypeptide of the invention. The non-coding regions ("5' and 3' untranslated regions") are the 5' and 3' sequences which flank the coding region and are not translated into amino acids. An antisense oligonucleotide can be, for example, about 5, 10, 15, 20, 25, 30, 35, 40, 45, or 50 or more nucleotides in length. An antisense nucleic acid of the invention can be constructed using chemical synthesis and enzymatic ligation reactions using procedures known in the art. The antisense nucleic acid molecules of the invention are typically administered to a subject or generated in situ such that they hybridize with or bind to cellular mRNA and/or genomic DNA encoding a polypeptide corresponding to a selected marker of the invention to thereby inhibit expression of the marker, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. Examples of a route of administration of antisense nucleic acid molecules of the invention includes direct injection at a tissue site or infusion of the antisense nucleic acid into a blood- or bone marrow-associated body fluid. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the invention can be an α-anomeric nucleic acid molecule. An α-anomeric nucleic acid molecule forms specific double-stranded hybrids with complementary RNA in which, contrary to the usual α-units, the strands run parallel to each other (Gaultier et al., 1987, *Nucleic Acids Res.* 15:6625-6641). The antisense nucleic acid molecule can also comprise a 2'-o-methylribonucleotide (Inoue et al., 1987, *Nucleic Acids Res.* 15:6131-6148) or a chimeric RNA-DNA analogue (Inoue et al., 1987, *FEBS Lett.* 215:327-330).

An "RNA interfering agent" as used herein, is defined as any agent which interferes with or inhibits expression of a target gene, e.g., a marker of the invention, by RNA interference (RNAi). Such RNA interfering agents include, but are not limited to, nucleic acid molecules including RNA molecules which are homologous to the target gene, e.g., a marker of the invention, or a fragment thereof, short interfering RNA (siRNA), and small molecules which interfere with or inhibit expression of a target gene by RNA interference (RNAi).

"RNA interference (RNAi)" is an evolutionarily conserved process whereby the expression or introduction of RNA of a sequence that is identical or highly similar to a target gene results in the sequence specific degradation or specific post-transcriptional gene silencing (PTGS) of messenger RNA (mRNA) transcribed from that targeted gene (see Coburn, G. and Cullen, B. (2002) *J. of Virology* 76(18): 9225), thereby inhibiting expression of the target gene (see, e.g., U.S. Patent Application Nos: 20030153519A1; 20030167490A1; and U.S. Pat. Nos. 6,506,559; 6,573,099, which are herein incorporated by reference in their entirety). In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs. siRNAs are incorporated into a protein complex that recognizes and cleaves target mRNAs. RNAi can also be initiated by introducing nucleic acid molecules, e.g., synthetic siRNAs or RNA interfering agents, to inhibit or silence the expression of target genes. As used herein, "inhibition of target gene expression" or "inhibition of marker gene expression" includes any decrease in expression or protein activity or level of the target gene (e.g., a marker gene of the invention) or protein encoded by the target gene, e.g., a marker protein of the invention. The decrease may be of at least 30%, 40%, 50%, 60%, 70%, 80%, 90%, 95% or 99% or more as compared to the expression of a target gene or the activity or level of the protein encoded by a target gene which has not been targeted by an RNA interfering agent.

The present invention also contemplates "short interfering RNA" (siRNA), also referred to herein as "small interfering RNA." Such a molecule is defined as an agent which functions to inhibit expression of a target gene, e.g., by RNAi. As used herein, the term siRNA is intended to be equivalent to any term in the art defined as a molecule capable of mediating sequence-specific RNAi. Such equivalents include, for example, double-stranded RNA (dsRNA), microRNA (mRNA), short hairpin RNA (shRNA), short interfering oligonucleotide, and post-transcriptional gene silencing RNA (ptgsRNA). An siRNA may be chemically synthesized, may be produced by in vitro transcription, or may be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, or 22 nucleotides in length, and may contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA).

In another embodiment, an siRNA is a small hairpin (also called stem loop) RNA (shRNA). In one embodiment, these shRNAs are composed of a short (e.g., 19-25 nucleotide) antisense strand, followed by a 5-9 nucleotide loop, and the analogous sense strand. Alternatively, the sense strand may precede the nucleotide loop structure and the antisense strand may follow. These shRNAs may be contained in plasmids, retroviruses, and lentiviruses and expressed from, for example, the pol III U6 promoter, or another promoter (see, e.g., Stewart, et al. (2003) *RNA* Apr; 9(4):493-501 incorporated by reference herein).

RNA interfering agents, e.g., siRNA molecules, may be administered to a subject having or at risk for having cancer, to inhibit expression of a marker gene of the invention, e.g., a marker gene which is overexpressed in cancer (such as the markers listed in Table 3) and thereby treat, prevent, or inhibit cancer in the subject.

The present invention also encompasses ribozymes. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes as described in Haselhoff and Gerlach, 1988, *Nature* 334:585-591) can be used to catalytically cleave mRNA transcripts to thereby inhibit translation of the protein encoded by the mRNA. A ribozyme having specificity for a nucleic acid molecule encoding a target polypeptide can be designed based upon the nucleotide sequence of a cDNA corresponding to the marker. For example, a derivative of a *Tetrahymena* L-19 IVS RNA can be constructed in which the nucleotide sequence of the active site is complementary to the nucleotide sequence to be cleaved (see Cech et al. U.S. Pat. No. 4,987,071; and Cech et al. U.S. Pat. No. 5,116,742). Alternatively, an mRNA encoding a polypeptide of the invention can be used to select a catalytic RNA having a specific ribonuclease activity from a pool of RNA molecules (see, e.g., Bartel and Szostak, 1993, *Science* 261: 1411-1418).

The present invention also encompasses nucleic acid molecules which form triple helical structures. For example, expression of a polypeptide of the invention can be inhibited by targeting nucleotide sequences complementary to the regulatory region of the gene encoding the polypeptide (e.g., the promoter and/or enhancer) to form triple helical structures that prevent transcription of the gene in target cells. See generally Helene (1991) *Anticancer Drug Des.* 6(6):569-84; Helene (1992) *Ann. N.Y. Acad. Sci.* 660:27-36; and Maher (1992) *Bioassays* 14(12):807-15.

In various embodiments, nucleic acid molecules can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acid molecules (see Hyrup et al., 1996, *Bioorganic & Medicinal Chemistry* 4(1): 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) *Proc. Natl. Acad. Sci. USA* 93:14670-675.

PNAs can be used in therapeutic and diagnostic applications. For example, PNAs can be used as antisense or antigene agents for sequence-specific modulation of gene expression by, e.g., inducing transcription or translation arrest or inhibiting replication. PNAs can also be used, e.g., in the analysis of single base pair mutations in a gene by, e.g., PNA directed PCR clamping; as artificial restriction enzymes when used in combination with other enzymes, e.g., S1 nucleases (Hyrup (1996), supra; or as probes or primers for DNA sequence and hybridization (Hyrup, 1996, supra; Perry-O'Keefe et al., 1996, *Proc. Natl. Acad. Sci. USA* 93:14670-675).

In another embodiment, PNAs can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be generated which can combine the advantageous properties of PNA and DNA. Such chimeras allow DNA recognition enzymes, e.g., RNASE H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup, 1996, supra). The synthesis of PNA-DNA chimeras can be performed as described in Hyrup (1996), supra, and Finn et al. (1996) *Nucleic Acids Res.* 24(17):3357-63. For example, a DNA chain can be synthesized on a solid support using standard phosphoramidite coupling chemistry and modified nucleoside analogs. Compounds such as 5'-(4-methoxytrityl)amino-5'-deoxy-thymidine phosphoramidite can be used as a link between the PNA and the 5' end of DNA (Mag et al., 1989, *Nucleic Acids Res.* 17:5973-88). PNA monomers are then coupled in a step-wise manner to produce a chimeric molecule with a 5' PNA segment and a 3' DNA segment (Finn et al., 1996, *Nucleic Acids Res.* 24(17):3357-63). Alternatively, chimeric molecules can be synthesized with a 5' DNA segment and a 3' PNA segment (Peterser et al., 1975, *Bioorganic Med. Chem. Lett.* 5:1119-11124).

In other embodiments, the oligonucleotide can include other appended groups such as peptides (e.g., for targeting host cell receptors in vivo), or agents facilitating transport across the cell membrane (see, e.g., Letsinger et al., 1989, *Proc. Natl. Acad. Sci. USA* 86:6553-6556; Lemaitre et al., 1987, *Proc. Natl. Acad. Sci. USA* 84:648-652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al., 1988, *Bio/Techniques* 6:958-976) or intercalating agents (see, e.g., Zon, 1988, *Pharm. Res.* 5:539-549). To this end, the oligonucleotide can be conjugated to another molecule, e.g., a peptide, hybridization triggered cross-linking agent, transport agent, hybridization-triggered cleavage agent, etc.

The present invention also includes molecular beacon nucleic acid molecules having at least one region which is complementary to a nucleic acid molecule of the invention, such that the molecular beacon is useful for quantitating the presence of the nucleic acid molecule of the invention in a sample. A "molecular beacon" nucleic acid is a nucleic acid molecule comprising a pair of complementary regions and having a fluorophore and a fluorescent quencher associated therewith. The fluorophore and quencher are associated with different portions of the nucleic acid in such an orientation that when the complementary regions are annealed with one another, fluorescence of the fluorophore is quenched by the quencher. When the complementary regions of the nucleic acid molecules are not annealed with one another, fluorescence of the fluorophore is quenched to a lesser degree. Molecular beacon nucleic acid molecules are described, for example, in U.S. Pat. No. 5,876,930.

In addition, aptamers are contemplated and can be produced using the methodology disclosed in a U.S. Pat. No. 5,270,163 and WO 91/19813.

The present invention also pertains to isolated proteins which correspond to pro-survival signaling pathway targets and/or appropriately enhance or inhibit the activity of such targets and biologically active portions thereof. In one embodiment, the native polypeptide corresponding to a biomarker can be isolated from cells or tissue sources by an appropriate purification scheme using standard protein purification techniques. In another embodiment, polypeptides corresponding to a biomarker of the invention are produced by recombinant DNA techniques. Alternative to recombinant expression, a polypeptide corresponding to a biomarker of the invention can be synthesized chemically using standard peptide synthesis techniques. Biologically active portions of a polypeptide corresponding to a biomarker of the invention include polypeptides comprising amino acid sequences sufficiently identical to or derived from the amino acid sequence of the protein corresponding to the biomarker which include fewer amino acids than the full length protein, and exhibit at least one activity of the corresponding full-length protein. Typically, biologically active portions comprise a domain or motif with at least one activity of the corresponding protein. A biologically active portion of a protein of the invention can be a polypeptide which is, for example, 10, 25, 50, 100 or more amino acids in length. Moreover, other biologically active portions, in which other regions of the protein are deleted, can be prepared by recombinant techniques and evaluated for one or more of the functional activities of the native form of a polypeptide of the invention.

Preferred polypeptides have an amino acid sequence of a protein encoded by a nucleic acid molecule encoding the target. Other useful proteins are substantially identical (e.g., at least about 40%, preferably 50%, 60%, 70%, 80%, 90%, 95%, or 99%) to one of these sequences and retain the functional activity of the protein of the corresponding naturally-occurring protein yet differ in amino acid sequence due to natural allelic variation or mutagenesis.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In one embodiment the two sequences are the same length.

The determination of percent identity between two sequences can be accomplished using a mathematical algorithm. A preferred, non-limiting example of a mathematical algorithm utilized for the comparison of two sequences is the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877. Such an algorithm is incorporated into the NBLAST and XBLAST programs of Altschul, et al. (1990) *J. Mol. Biol.* 215:403-410. BLAST nucleotide searches can be performed with the NBLAST program, score=100, word length=12 to obtain nucleotide sequences homologous to a nucleic acid molecules of the invention. BLAST protein searches can be performed with the XBLAST program, score=50, word length=3 to obtain amino acid sequences homologous to a protein molecules of the invention. To obtain gapped alignments for comparison purposes, Gapped BLAST can be utilized as described in Altschul et al. (1997) *Nucleic Acids Res.* 25:3389-3402. Alternatively, PSI-Blast can be used to perform an iterated search which detects distant relationships between molecules. When utilizing BLAST, Gapped BLAST, and PSI-Blast programs, the default parameters of the respective programs (e.g., XBLAST and NBLAST) can be used. See http://www.ncbi.nlm.nih.gov. Another preferred, non-limiting example of a mathematical algorithm utilized for the comparison of sequences is the algorithm of Myers and Miller, (1988) *Comput Appl Biosci,* 4:11-7. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson and Lipman (1988) *Proc. Natl. Acad. Sci. USA* 85:2444-2448. When using the FASTA algorithm for comparing nucleotide or amino acid sequences, a PAM120 weight residue table can, for example, be used with a k-tuple value of 2.

The percent identity between two sequences can be determined using techniques similar to those described above, with or without allowing gaps. In calculating percent identity, only exact matches are counted.

The invention also provides chimeric or fusion proteins. As used herein, a "chimeric protein" or "fusion protein" comprises all or part (preferably a biologically active part) of a polypeptide corresponding to a biomarker of the invention operably linked to a heterologous polypeptide (i.e., a polypeptide other than the polypeptide corresponding to the biomarker). Within the fusion protein, the term "operably linked" is intended to indicate that the polypeptide of the invention and the heterologous polypeptide are fused in-frame to each other. The heterologous polypeptide can be fused to the amino-terminus or the carboxyl-terminus of the polypeptide of the invention. Such fusion proteins are well known in the art and include, for example, target proteins or polypeptides that enhance or inhibit the activity of such target proteins fused to heterologous signal sequences, peptide tags, immunoglobulin fusion proteins, and the like. Chimeric and fusion proteins of the invention can be produced by standard recombinant DNA techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see, e.g., Ausubel et al., supra). Moreover, many expression vectors are commercially available that already encode a fusion moiety (e.g., a GST polypeptide). A nucleic acid encoding a polypeptide of the invention can be cloned into such an expression vector such that the fusion moiety is linked in-frame to the polypeptide of the invention.

The present invention also pertains to variants of the polypeptides. Such variants have an altered amino acid sequence which can function as either agonists (mimetics) or as antagonists. Variants can be generated by mutagenesis, e.g., discrete point mutation or truncation. An agonist can retain substantially the same, or a subset, of the biological activities of the naturally occurring form of the protein. An antagonist of a protein can inhibit one or more of the activities of the naturally occurring form of the protein by, for example, competitively binding to a downstream or upstream member of a cellular signaling cascade which includes the protein of interest. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the protein.

Variants of a protein of the invention which function as either agonists (mimetics) or as antagonists can be identified by screening combinatorial libraries of mutants, e.g., truncation mutants, of the protein of the invention for agonist or antagonist activity. In one embodiment, a variegated library of variants is generated by combinatorial mutagenesis at the nucleic acid level and is encoded by a variegated gene library. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (e.g., for phage display). There are a variety of methods which can be used to produce libraries of potential variants of the polypeptides of the invention from a degenerate oligonucleotide sequence. Methods for synthesizing degenerate oligonucleotides are known in the art (see, e.g., Narang, 1983, *Tetrahedron* 39:3; Itakura et al., 1984, *Annu. Rev. Biochem.* 53:323; Itakura et al., 1984, *Science* 198: 1056; Ike et al., 1983 *Nucleic Acid Res.* 11:477).

In addition, libraries of fragments of the coding sequence of a polypeptide corresponding to a biomarker of the invention can be used to generate a variegated population of polypeptides for screening and subsequent selection of variants. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes amino terminal and internal fragments of various sizes of the protein of interest.

Several techniques are known in the art for screening gene products of combinatorial libraries made by point mutations or truncation, and for screening cDNA libraries for gene products having a selected property. The most widely used techniques, which are amenable to high throughput analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a protein of the invention (Arkin and Yourvan, 1992, *Proc. Natl. Acad. Sci. USA* 89:7811-7815; Delgrave et al., 1993, *Protein Engineering* 6(3):327-331).

Also contemplated are antibodies that bind to pro-survival signaling pathway targets to thereby appropriately enhance or inhibit their activity. An isolated target polypeptide or a fragment thereof (or a nucleic acid encoding such a polypeptide), can be used as an immunogen to generate antibodies that bind to said immunogen, using standard techniques for polyclonal and monoclonal antibody preparation.

Unless otherwise specified herein, the terms "antibody" and "antibodies" broadly encompass naturally-occurring forms of antibodies (e.g. IgG, IgA, IgM, IgE) and recombinant antibodies such as single-chain antibodies, chimeric and humanized antibodies and multi-specific antibodies, as well as fragments and derivatives of all of the foregoing, which fragments and derivatives have at least an antigenic binding site. Antibody derivatives may comprise a protein or chemical moiety conjugated to an antibody.

The term "antibody" as used herein also includes an "antigen-binding portion" of an antibody (or simply "antibody portion"). The term "antigen-binding portion", as used herein, refers to one or more fragments of an antibody that retain the ability to specifically bind to a target antigen. It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent polypeptides (known as single chain Fv (scFv); see e.g., Bird et al. (1988) *Science* 242:423-426; and Huston et al. (1988) *Proc. Natl. Acad. Sci. USA* 85:5879-5883; and Osbourn et al. 1998, Nature Biotechnology 16: 778). Such single chain antibodies are also intended to be encompassed within the term "antigen-binding portion" of an antibody. Any VH and VL sequences of specific scFv can be linked to human immunoglobulin constant region cDNA or genomic sequences, in order to generate expression vectors encoding complete IgG polypeptides or other isotypes. VH and VL can also be used in the generation of Fab, Fv or other fragments of immunoglobulins using either protein chemistry or recombinant DNA technology. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak, R. J., et al. (1994) *Structure* 2:1121-1123).

Still further, an antibody or antigen-binding portion thereof may be part of larger immunoadhesion polypeptides, formed by covalent or noncovalent association of the antibody or antibody portion with one or more other proteins or peptides. Examples of such immunoadhesion polypeptides include use of the streptavidin core region to make a tetrameric scFv polypeptide (Kipriyanov, S. M., et al. (1995) *Human Antibodies and Hybridomas* 6:93-101) and use of a cysteine residue, a marker peptide and a C-terminal polyhistidine tag to make bivalent and biotinylated scFv polypeptides (Kipriyanov, S. M., et al. (1994) *Mol. Immunol.* 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion polypeptides can be obtained using standard recombinant DNA techniques, as described herein.

Antibodies may be polyclonal or monoclonal; xenogeneic, allogeneic, or syngeneic; or modified forms thereof (e.g., humanized, chimeric, etc.). Antibodies may also be fully human. Preferably, antibodies of the invention bind specifically or substantially specifically to pro-survival signaling pathway polypeptides of interest or fragments thereof. The terms "monoclonal antibodies" and "monoclonal antibody composition", as used herein, refer to a population of antibody polypeptides that contain only one species of an antigen binding site capable of immunoreacting with a particular epitope of an antigen, whereas the term "polyclonal antibodies" and "polyclonal antibody composition" refer to a population of antibody polypeptides that contain multiple species of antigen binding sites capable of interacting with a particular antigen. A monoclonal antibody composition typically displays a single binding affinity for a particular antigen with which it immunoreacts.

C. Pharmaceutical Compositions

In another aspect, the present invention provides pharmaceutically acceptable compositions which comprise a therapeutically-effective amount of agents described herein, e.g., a chemotherapeutic agent, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The term "administering" is intended to include routes of administration which allow the compositions described herein to perform their intended functions of treating cancer or inhibiting cancer cell growth. Examples of routes of administration which can be used include injection (subcutaneous, intravenous, parenterally, intraperitoneally, intrathecal, etc.), oral, inhalation, and transdermal. The injection can be bolus injections or can be continuous infusion. Depending on the route of administration, the therapeutic agents can be coated with or disposed in a selected material to protect it from natural conditions which may detrimentally effect its ability to perform its intended function. The therapeutic agents can be administered alone, or in conjunction with a pharmaceutically acceptable carrier. Further the therapeutic agents can be administered as a mixture of therapeutic agents, which also can be coadministered with a pharmaceutically acceptable carrier.

As used herein, an "effective amount," when used with respect to the combination of agents described herein includes, without limitation, an amount of each agent in the combination that provides a statistically significant desired effect on cancer cells. In some embodiments, the effect amount can be narrowed to further require clinical acceptability of the amount of toxicity to non-cancer cells. Representative desired effects are described herein. For example, the effect can be a decrease in the rate of tumor growth, a cessation of tumor growth, or a reduction in the size, mass, metabolic activity, or volume of the tumor, as measured by standard criteria such as, but not limited to, the Response Evaluation Criteria for Solid Tumors (RECIST), a statistically significant increase in survival relative to treatment with individual agents of the combination or subcombinations of the combination alone, and the like. The effective amount can vary depending on such factors as the type of cell growth being treated or inhibited, the type of therapeutic agent(s) employed, the particular therapeutic agent, the size of the subject, or the severity of the cancer cell growth or tumor. For example, the choice of each of the individual agents which make up the combination can affect what constitutes an "effective amount". One of ordinary skill in the art would be able to study the aforementioned factors and make the determination regarding the effective amount of the combination of the therapeutic agents without undue experimentation.

For example, an in vitro assay can be used to determine an "effective amount" of the therapeutic agents. The ordinarily skilled artisan would select an appropriate amount of each individual agent in the combination for use in the aforementioned in vitro assay. The cell survival fraction can be used to determine whether the selected amounts were an "effective amount" for the particular combination of therapeutic agents. For example, the selected amounts used within the assay preferably should result in a killing of at least 50% of the cells, more preferably 75%, and most preferably at least 95%. In a preferred embodiment, the effective dose of the therapeutic agent is a subtoxic dose. As used herein, the term subtoxic dose refers to a dose which results in the killing of less than about 10% of the cells.

The regimen (e.g., order) of administration can also affect what constitutes an effective amount. Further, several divided dosages, as well as staggered dosages, can be administered daily or sequentially, or the dose can be continuously infused. Further, the dosages can be proportionally increased or decreased as indicated by the exigencies of the therapeutic situation.

The phrase "pharmaceutically acceptable" is employed herein to refer to those combinations of therapeutic agents, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically-acceptable salts" refers to the relatively non-toxic, inorganic and organic acid addition salts of the therapeutic agents encompassed by the invention. These salts can be prepared in situ during the final isolation and purification of the therapeutic agents, or by separately reacting a purified therapeutic agents in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1-19)

In other cases, the therapeutic agents useful in the methods of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of therapeutic agents. These salts can likewise be prepared in situ during the final isolation and purification of the therapeutic agents, or by separately reacting the purified therapeutic agents in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations useful in the methods of the present invention include those suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a therapeutic agent with the carrier and, optionally, one or more accessory ingredients. In general, the formulations are prepared by uniformly and intimately bringing into association a therapeutic agent with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a therapeutic agent as an active ingredient. A compound may also be administered as a bolus, electuary or paste.

In solid dosage forms for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered peptide or peptidomimetic moistened with an inert liquid diluent.

Tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active therapeutic agents may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more therapeutic agents with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Formulations which are suitable for vaginal administration also include pessaries, tampons, creams, gels, pastes, foams or spray formulations containing such carriers as are known in the art to be appropriate.

Dosage forms for the topical or transdermal administration of a therapeutic agent include powders, sprays, ointments, pastes, creams, lotions, gels, solutions, patches and inhalants. The active component may be mixed under sterile conditions with a pharmaceutically-acceptable carrier, and with any preservatives, buffers, or propellants which may be required.

The ointments, pastes, creams and gels may contain, in addition to a therapeutic agent, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a therapeutic agent, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The therapeutic agent can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a therapeutic agent to the body. Such dosage forms can be made by dissolving or dispersing the agent in the proper medium. Absorption enhancers can also be used to increase the flux of the peptidomimetic across the skin. The rate of such flux can be controlled by either providing a rate controlling membrane or dispersing the peptidomimetic in a polymer matrix or gel.

Ophthalmic formulations, eye ointments, powders, solutions and the like, are also contemplated as being within the scope of this invention.

Pharmaceutical compositions of this invention suitable for parenteral administration comprise one or more therapeutic agents in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of a therapeutic agent in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the therapeutic agents of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

III. Anti-Cancer Methods

The methods of the present invention relate to therapeutic and prophylactic compositions for treating cancer or preventing the growth of cancer cells, e.g., tumor growth in a subject. The compositions of the present invention include an effective amount of ceramide (e.g., C6-ceramide) and an effective amount of one or more anti-cancer agents. Other aspects of the present invention include compositions, such as packaged C6-ceramide and additional therapeutic agent(s). The packaged compounds and agents can also include instructions for using the composition for treating cancer or preventing the growth of cancer cells.

In another aspect, the invention relates to methods for treating cancer, e.g., inhibiting tumor growth, in a subject by administering to a subject an effective amount of a ceramide (e.g., C6-ceramide) and an effective amount of a therapeutic agent, e.g., a chemotherapeutic agent, wherein the ceramide allows for a reduction in the amount of the therapeutic agent(s) required to be effective, resulting in fewer side effects in the subject being treated.

In general, the methods of the present invention include a step of contacting cancer cells with a combination of a ceramide (e.g., C6-ceramide) and a therapeutic agent, e.g., a chemotherapeutic agent, effective for promoting apoptosis or cell death. In some embodiments, the cancer cells can harbor activating KRAS mutations. In other embodiments, the cancer cells do not harbor activating KRAS mutations.

As used herein, the term "cell death" includes the processes by which mammalian cells die or become terminally differentiated. Such processes include apoptosis (both reversible and irreversible) and processes thought to involve apoptosis (e.g., cell senescence), as well as necrosis and terminal cell differentiation. "Cell death" is used herein to refer to the death or imminent death of nucleated cells (e.g., neurons, myocytes, hepatocytes and the like) as well as to the death or imminent death of anucleate cells (e.g., red blood cells, platelets, and the like). Cell death is typically manifested by the exposure of the internal membrane phospholipid phosphatidylserine (PS) on the outer leaflet of the plasma membrane and can be detected by art recognized methods.

As used herein the term "apoptosis" includes programmed cell death which can also be detected using techniques which are known in the art. For example, apoptotic cell death can be characterized, e.g., by cell shrinkage, membrane blebbing and chromatin condensation culminating in cell fragmentation. Cells undergoing apoptosis also display a characteristic pattern of internucleosomal DNA cleavage. Apoptosis can be measured in the presence or the absence of Fas-mediated signals. In one embodiment, cytochrome C release from mitochondria during cell apoptosis can be detected, e.g., plasma cell apoptosis (as described in, for example, Bossy-Wetzel E. et al. (2000) *Methods in Enzymol.* 322:235-42). Other assays include: cytofluorometric quantitation of nuclear apoptosis induced in a cell-free system (as described in, for example, Lorenzo H. K. et al. (2000) *Methods in Enzymol.* 322:198-201); apoptotic nuclease assays (as described in, for example, Hughes F. M. (2000) *Methods in Enzymol.* 322:47-62); analysis of apoptotic cells, e.g., apoptotic plasma cells, by flow and laser scanning cytometry (as described in, for example, Darzynkiewicz Z. et al. (2000) *Methods in Enzymol.* 322:18-39); detection of apoptosis by annexin V labeling (as described in, for example, Bossy-Wetzel E. et al. (2000) *Methods in Enzymol.* 322:15-18); transient transfection assays for cell death genes (as described in, for example, Miura M. et al. (2000) *Methods in Enzymol.* 322:480-92); and assays that detect DNA cleavage in apoptotic cells, e.g., apoptotic plasma cells (as described in, for example, Kauffman S. H. et al. (2000) *Methods in Enzymol.* 322:3-15). Apoptosis can also be measured by propidium iodide staining or by TUNEL assay.

In another aspect, the invention features methods for inhibiting the proliferation of cancer cells by contacting the cells with a ceramide (e.g., C6-ceramide) and a therapeutic agent(s). In general, the method includes a step of contacting cancer cells with a ceramide (e.g., C6-ceramide) and a therapeutic agent(s) effective for reducing the proliferation of cancer cells. The reduced proliferation of cancer cells can be detected by at least one of the following biological activities: (1) a decrease in solid tumor cell proliferation; (2) a decrease in the fraction of cells in the DNA synthesis phase of the cell cycle (S-phase); (3) an increase in expression of differentiation-associated markers; (4) a decrease in the expression of proliferation-associated markers such as Ki-67 (MIB-1), e.g., a decrease in the expression of Ki-67 by about 30-50%, using techniques which are known in the art. Changes in expression can occur in the protein or mRNA levels.

The present method can be performed on cells in culture, e.g., ex vivo, or can be performed on cells present in an animal subject, e.g., as part of an in vivo therapeutic protocol. The therapeutic regimen can be carried out on a human or other animal subject.

The methods of the present invention allow for a reduction in the amount of the therapeutic agent, e.g., a chemotherapeutic agent, required to be effective, resulting in fewer side effects in the subject being treated.

In one embodiment, the cells to be treated are pancreatic cancer and/or colorectal cancer cells. For instance, the instant method can be carried out to prevent the proliferation of a pancreatic cancer and/or colorectal cancer cell tumor.

Determination of a therapeutically effective amount of a ceramide (e.g., C6-ceramide) and a therapeutically effective amount of a therapeutic agent, e.g., a chemotherapeutic agent, can be readily made by the physician (the "attending clinician"), as one skilled in the art, by the use of known techniques and by observing results obtained under analogous circumstances. The dosages may be varied depending upon the requirements of the patient in the judgment of the attending clinician, the severity of the condition being treated and the particular compound being employed. In determining the therapeutically effective amount or dose, a number of factors are considered by the attending clinician, including, but not limited to: the specific hyperplastic/neoplastic cell involved; pharmacodynamic characteristics of the particular agent and its mode and route of administration; the desired time course of treatment; the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the kind of concurrent treatment; and other relevant circumstances. U.S. Pat. No. 5,427,916, for example, describes method for predicting the effectiveness of antineoplastic therapy in individual patients, and illustrates certain methods which can be used in conjunction with the treatment protocols of the instant invention.

The effectiveness of any particular combination of a ceramide (e.g., C6-ceramide) with a therapeutic agent(s) to treat cancer can be monitored by comparing two or more samples obtained from a patient undergoing anti-cancer treatment. In general, it is preferable to obtain a first sample from the patient prior to beginning therapy and one or more samples during treatment. In such a use, a baseline of expression of cancer cells prior to therapy is determined and then changes in the baseline state of expression of cancer cells is monitored during the course of therapy. Alternatively, two or more successive samples obtained during treatment can be used without the need of a pre-treatment baseline sample. In such a use, the first sample obtained from the subject is used as a baseline for determining whether the expression of cancer cells is increasing or decreasing.

In general, when monitoring the effectiveness of a therapeutic treatment, two or more samples from the patient are examined. Preferably, three or more successively obtained samples are used, including at least one pretreatment sample.

EXAMPLES

Example 1

Materials and Methods Used in Examples 2-8

A. Chemicals and Reagents

C6-ceramide was provided by Avanti (Alabaster, AB, CN: 860506P). paclitaxel and gemcitabine were obtained from the pharmacy at Roger Williams Medical Center. LY 294002. Rapamycin and U0126 were purchased from CalbioChem (San Diego, Calif.). ERK1/2, AKT1/2, goat anti-rabbit IgG-HRP and goat anti-mouse IgG-HRP antibodies were purchased from Santa Cruz Biotechnology (Santa Cruz, Calif.). Monoclonal mouse anti-βactin was obtained from Sigma (St. Louis, Mo.). p-AKT (S473), p-AKT (T308), p-S6K (Thr389), p-4E-BP1 (S65), p-4E-BP1 (T37/46), p-S6 (S235/236), p-GSKα/β (Ser21/P), p-ERK1/2 (T202/Y204) antibody were purchased from Cell Signaling Technology (Beverly, Mass.).

B. Cell Culture

Pancreatic cancer cell lines L3.6, PanC-1 and MIA-PaCa2 cells (MIA) were maintained in DMEM medium (Sigma, St. Louis, Mo.), supplemented with a 10% fetal bovine serum (Invitrogen, Carlsbad, Calif.), Penicillin/Streptomycin (1:100, Sigma, St. Louis, Mo.) and 4 mM L-glutamine (Sigma, St. Louis, Mo.), in a $CO_2$ incubator at 37° C. For Western blot analysis, cells were reseeded in 6-well plates at a density of $0.5 \times 10^6$ cells/ml with fresh complete culture medium.

C. Cell Viability Assay

Cell viability was measured by the 3-[4m5-dimethylthylthiazol-2-y]-2,5 diphenyltetrazolium bromide (MTT) method, as described in Cao et al. (2009) *Sci. Signal.* 2:RA17. Briefly, the cells were collected and seeded in 96-well plate at a density of $2 \times 10^5$ cells/cm$^2$. Different seeding densities were optimized at the beginning of the experiments. After overnight incubation cells were exposed to fresh medium containing indicated reagents at 37° C. After incubation for different time periods, 20 ul of MTT tetrazolium (Sigma, St. Louis, Mo.) salt dissolved in Hank's balanced salt solution at a concentration of 5 mg/ml was added to each well and incubated in a $CO_2$ incubator for an additional 4 hours. The medium was subsequently aspirated from each well and 150 ul of DMSO (Sigma, St. Louis, Mo.) was added to dissolve formazan crystals and the absorbance of each well was obtained using a Dynatech MR5000 plate reader at a test wavelength of 490 nm with a reference wavelength of 630 nm.

D. Western Blot

As described in Cao et al. (2009) *Sci. Signal.* 2:RA17, aliquots of 30-40 µg of protein from each sample (treated as indicated in the legends) were separated by 10% SDS-polyacrylamide gel electrophoresis (SDS-PAGE) and transferred onto a polyvinylidene difluoride (PVDF) membrane (Millipore, Bedford, Mass.). After blocking with 10% instant nonfat dry milk for 1 hour, membranes were incubated with specific antibodies overnight at 4° C. followed by incubation with secondary antibodies (HRP-conjugated anti-rabbit or anti-mouse IgG at the appropriate dilutions) for 60 minutes to 1 hour at room temperature. Antibody binding was detected with the enhanced chemiluminescence (ECL) detection system (Amersham Biosciences, Piscataway, N.J.).

E. In Vivo Human Pancreatic Tumor Mice Xenograft Model

SCID/Beige/Taconic male mice were inoculated with $2 \times 10^6$ L3.6 pancreatic cells and treated for 4 days post tumor implant with thrice weekly (3×/wk) intraperitoneal (I.P.) injections of paclitaxel (taxol) 3.0 mg/ml or gemcitabine (Gem) 10 mg/ml-after treatment and were autopsied when near death (as per IRB committee). Mouse survival, tumor volume (in cm$^3$), and body weight (in grams) were recorded.

Average rate of tumor development was calculated by dividing total tumor volume by total number of days monitored.

Example 2

C6-Ceramide Dramatically Enhances Paclitaxel (Taxol) Induced Cell Death in L3.6 Pancreatic Cancer Cells In Vitro Synergism of paclitaxel and C6-ceramide in killing L3.6 cells in vitro was tested using an MTT assay in which cell death was reflected as reduced MTT value. C6-ceramide, which alone has limited effects in inducing on L3.6 cell death, dramatically enhanced paclitaxel induced cell death in a dose dependent manner (FIGS. 1A and 1C). For example, 1.5 µg/ml of paclitaxel killed less than 5%, but combination therapy caused more than 90% of L3.6 cell death. Importantly, when L3.6 cells were cultured in 10% FBS, neither taxol or C6-ceramide alone had any meaningful effects on L3.6 cell death, whereas a combination of those two agents at a very low concentration caused a significant cell death (FIGS. 1B and 1D). For example, 2.5 µg/ml of C6-ceramide plus 1.5 µg/ml of taxol caused more than 70% cell death of L3.6 cells, while neither of these two alone had any measurable effect on L3.6 cell death when cultured in 10% FBS. Thus, synergism between the two agents was demonstrated.

Example 3

C6-Ceramide and Taxol Induce Synergistic Anti-Tumor Effect In Vivo

Figure 2:
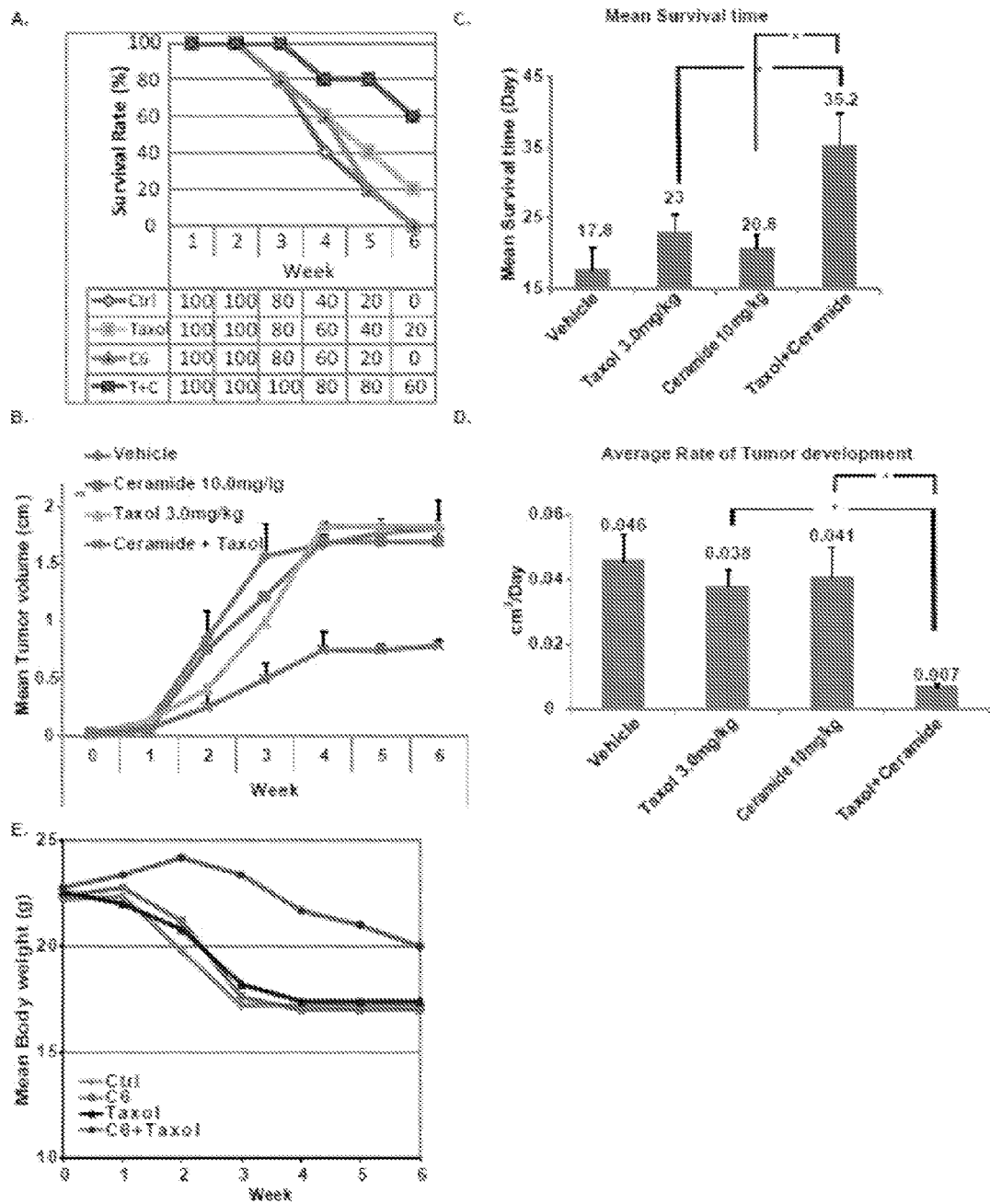
FIGS. 2A-2E show that C6-ceramide and paclitaxel cause synergistic anti-tumor effects in vivo. SCID/Beige/Taconic nude male mice, 22-25 g, 6-8 weeks old were ear tagged and randomized into 4 different groups (Control, ceramide, paclitaxel, ceramide+paclitaxel) of 5 mice each prior to inoculation subcutaneously (s.c.) with 2×10$^6$ L3.6 cells in a volume 0.1 ml into the internal surface of the right thigh. Treatment was started 4 days after L3.6 cell injection with thrice weekly (3×/wk) intraperitoneal (i.p.) injections of paclitaxel 3.0 mg/ml with or without C6-ceramide (10 mg/ml) for 2 weeks. Mouse survival (FIGS. 2A and 2C), tumor volume (in cm$^3$.

As discussed in Example 2, C6-ceramide and taxol exhibited significant synergism in inducing L3.6 cancer cell death in vitro. Whether possible synergistic anti-tumor effects between these two in vivo also occurred was subsequently determined using the heterotransplanted L3.6 cell model in SCID mice. As shown in FIGS. 2A and 2B, only the group that received combination taxol (3 mg/ml) and C6-ceramide (10 mg/ml) treatment showed significantly smaller tumor volumes and enhanced mouse survival as compared to the control treatment group and the groups that received single treatment taxol (3 mg/ml) or C6-ceramide (10 mg/ml). The control and single agent treatments had minimal effects on tumor volume or mouse survival (FIGS. 2A and 2B). The average rate of tumor development was reduced to 0.0007 $cm^3$/day in the group receiving both taxol plus C6-ceramide treatment compared to 0.046 $cm^3$/day in the control groups (FIG. 2C). Further, the mean survival was extended to 35.2 days in the group receiving combined therapy (taxol/C6-ceramide) compared to 17.8 days in control group (FIG. 2D). The body weight of mice that received combined treatment was actually better than the control or individual agent treatment groups indicating relative safety of this strategy (FIG. 2E).

Example 4

Figure 3:
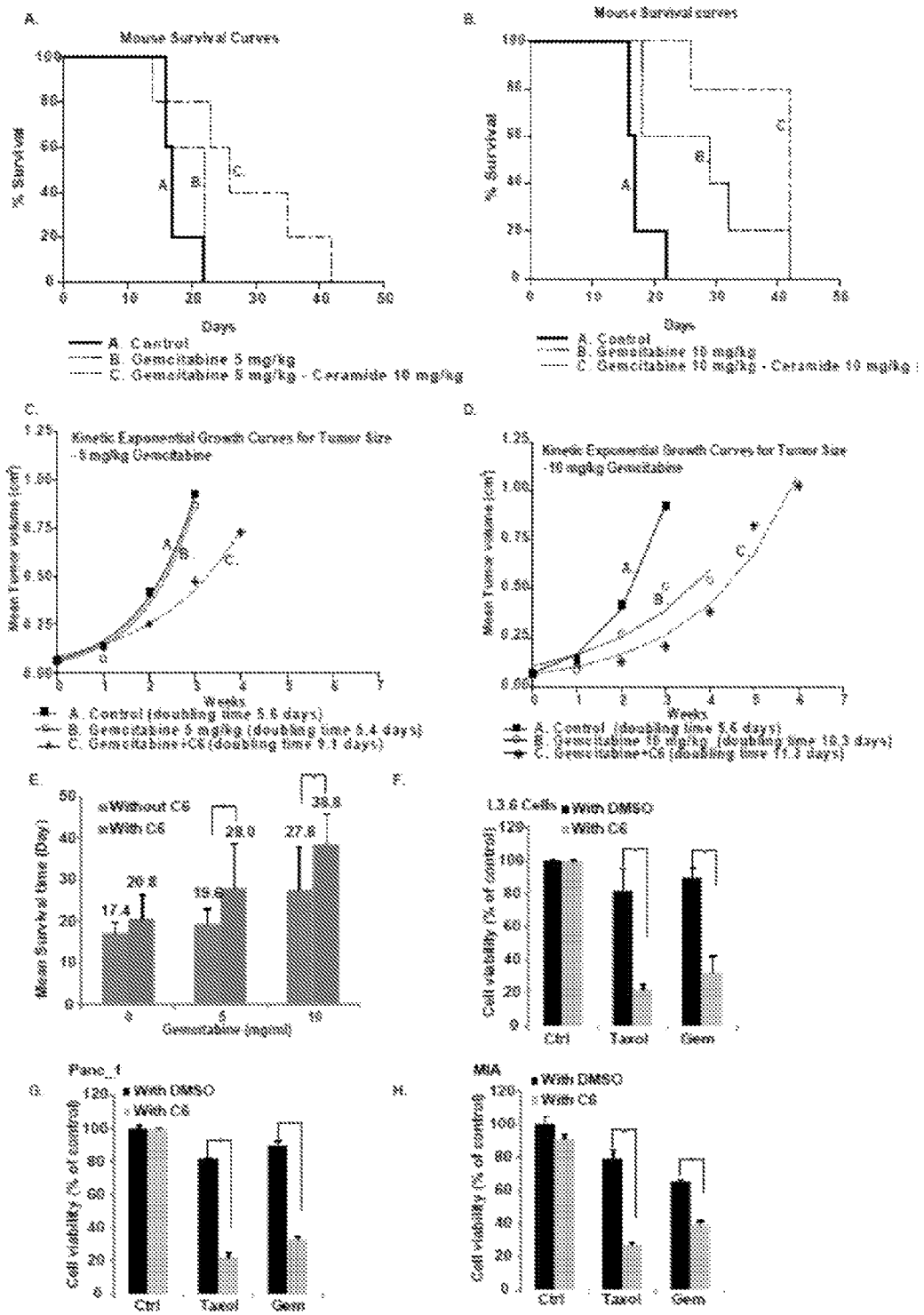
FIGS. 3A-3H show synergistic anti-tumor effects of C6-ceramide and gemcitabine in vivo and in vitro. SCID/Beige/Taconic nude male mice (22-25 g; 6-8 weeks old) were ear tagged and randomized into 4 different groups (Control, Ceramide, gemcitabine, Ceramide+gemcitabine) combining 5 mice each prior to inoculation subcutaneous (s.c.) with 2×10$^6$ L3.6 cells in a 0.1 ml volume into the internal surface of the right thigh. Treatment was started 4 days after L3.6 cell injection with thrice weekly (3×/wk) intraperitoneal (i.p.) injections of gemcitabine (two doses: 5.0 and 10.0 mg/ml) with or without C6-ceramide (10 mg/ml) for 2 weeks. Mouse survival (FIGS. 3A, 3B, and 3E)

Synergistic Anti-Tumor Effects of C6-Ceramide and Gemcitabine In Vivo and In Vitro The possible combination effect of C6-ceramide on gemcitabine-induced cytotoxicity (in vitro) and regression (in vivo) of the L3.6 pancreatic cancer cell was also tested according to the methods described in Examples 2 and 3. As shown in FIGS. 3A-3D, mice that received low dose gemcitabine treatment (5 mg/kg) had limited effect on survival and tumor growth. Increasing the dose of gemcitabine to 10 mg/kg caused a moderate anti-tumor effect in the L3.6 cells SCID mice model. For both doses, however, adding C6-ceramide (10 mg/ml) significantly increased the anti-tumor effects: significant tumor regression with overall reduced tumor size and significant prolongation of mice survival time in mice that received both C6-ceramide and gemcitabine treatment (FIG. 3E). A synergistic anti-tumor effect of gemcitabine and C6-ceramide in multiple pancreatic cancer cells in vitro was also determined. As shown in FIGS. 3F-3H, either gemcitabine (1.5 µg/ml) or C6-ceramide alone had moderate effect on cancer cell death, whereas the combination of these two agents caused a dramatic increase in cell death in pancreatic cancer cell lines L3.6 (FIG. 3F), Panc-1 (FIG. 3G), and MIA cells (FIG. 3H).

Example 5

Figure 4:
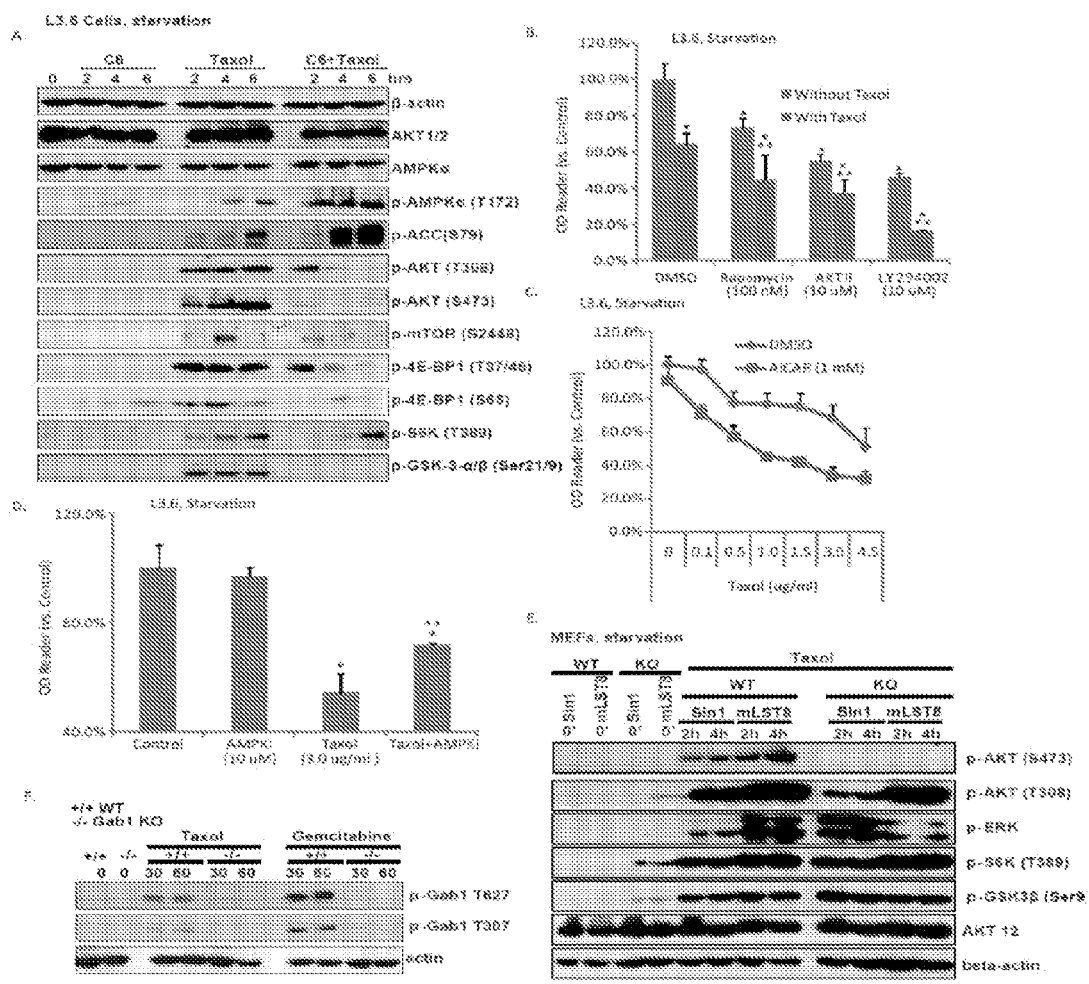
FIGS. 4A-4F show that PI3K/AKT/mTOR inhibition and AMPK activation enhance taxol induced cancer cell death.

PI3K/AKT/mTOR Inhibition and AMPK Activation Enhance Taxol Induced Cancer Cell Death The molecular mechanism involved in C6-ceramide induced chemosensitization effects was examined by focusing on taxol. Taxol alone is able to strongly induce PI3K/AKT/mTOR and AMPK activation. PI3K/AKT/mTOR inhibition by inhibitors (LY 294002 for PI3K/AKT inhibitor II for AKT and rapamycin for mTOR) and AMPK activation by selective activator (AICAR) enhance Taxol induced cancer cell death (FIGS. 4A-4C). AMPK inhibitors, on the other hand, protect cancer cells from Taxol-induced cell death (FIG. 4D). C6-ceramide dramatically reduces taxol induced pro-survival PI3K/AKT/mTOR pathway while enhancing pro-apoptotic pathway AMPK/ACC signaling (FIG. 4A). The data in FIG. 6E suggest that mTORC2 is required for Taxol induced AKT phosphorylation, since SIN1 or mLST8 knockout abolishes AKT phosphorylation.

Example 6

Figure 5:
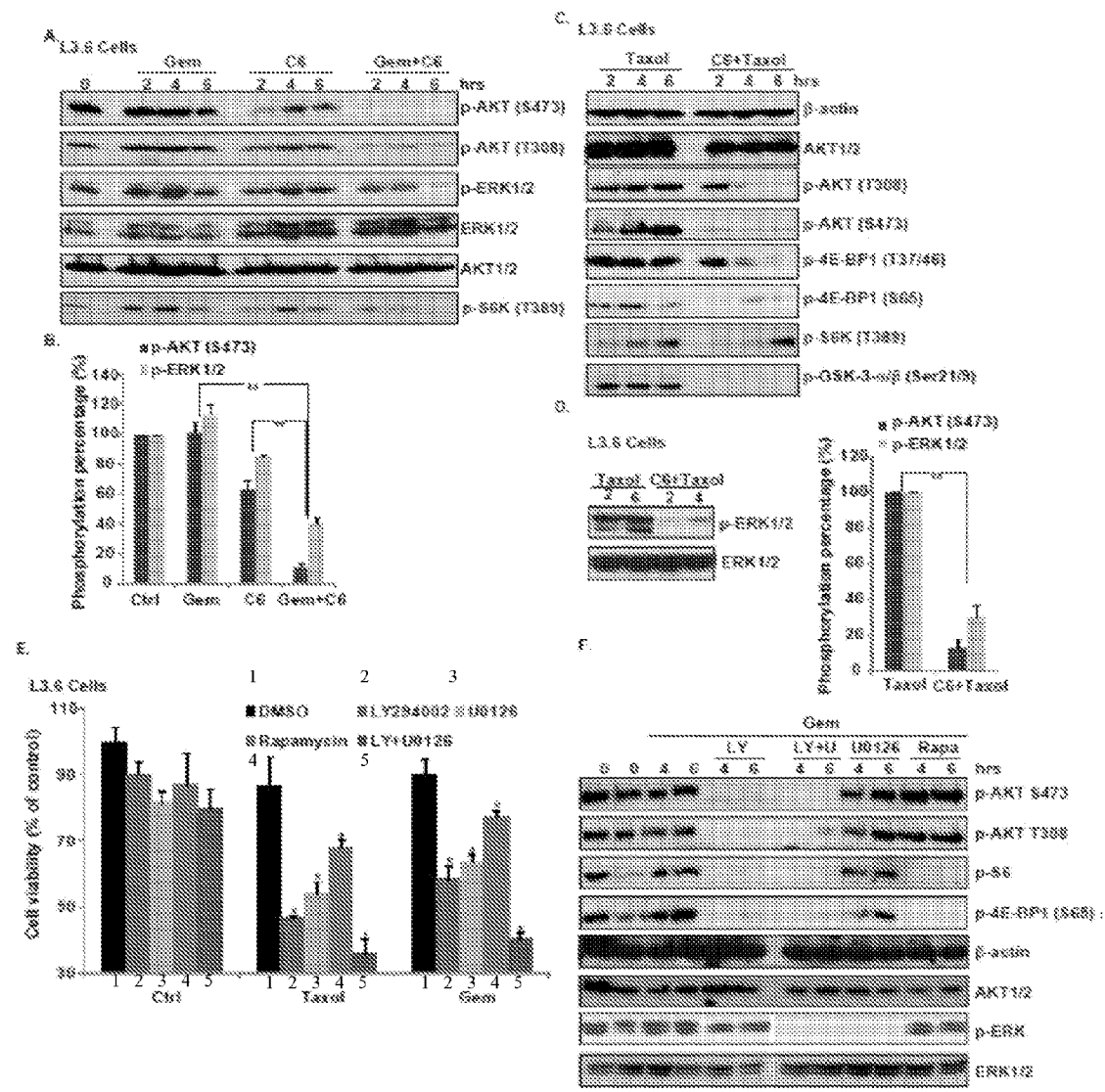
FIG. 5A-5F show that C6-ceramide plus gemcitabine or taxol causes inactivation of AKT/mTORC1 and ERK in vitro. Pancreatic cancer cell line L3.6 cells were left untreated or treated with gemcitabine (Gem, 1 µg/ml) or taxol (1.5 µg/ml) in the presence or absence of C6-ceramide (10 µg/ml) for 2, 4 and 6 hours, AKT/mTORC1 and ERK activation were detected by Western Blot using indicated antibodies (FIGS. 5A and 5C). p-AKT (S473) and p-ERK at 4 hour time intervals for each treatment quantified (FIGS. 5B and 5D). L3.6 cells were pretreated with various inhibitors including P13K/AKT inhibitor LY 294002 (LY, 1 µM), mTORC1 inhibitor rapamycin (100 nM), MEK/ERK inhibitor U0126 (1 µg/ml) or gemcitabine (1 µg/ml) for 48 hours, cell death was detected 48 hours later (FIG. 5E). The effects of the various inhibitors described above on AKT/mTORC1 and ERK activation were also detected by Western Blots using commercial available antibodies (FIG. 5F). *P<0.05 versus group without C6-ceramide presents. The experiments were repeated at least three times and similar results were observed.

Combination of C6-Ceramide with Gemcitabine or Taxol Synergistically Inactivates Prosurvival (KRAS Pathway) of AKT/mTORC1 and ERK In Vitro The effects of the observed synergistic effects of combination agents described in Examples 2-4 were extended by analyzing AKT/mTORC1 and ERK activation, which are two major pro-survival pathways in pancreatic cancer cell lines. As shown in FIG. 5A, gemcitabine itself had no effect on AKT/mTORC1 or ERK activation in the tested time period. C6-ceramide induced moderate survival of AKT/mTORC1 and ERK activation. However, treatment with a combination of gemcitabine and C6-ceramide caused a profound inhibition of both AKT/mTORC1 and ERK signaling (FIGS. 5A and 5B). AKT/mTORC1 or ERK signaling was also largely inhibited by combination treatment of taxol plus C6-ceramide (FIGS. 5C and 5D). These data together indicate that C6-ceramide plus gemcitabine or taxol causes in-activation of AKT/mTORC1 and ERK in vitro and may be the key mechanism to explain the observed synergistic anti-cancer effects.

Figure 6:
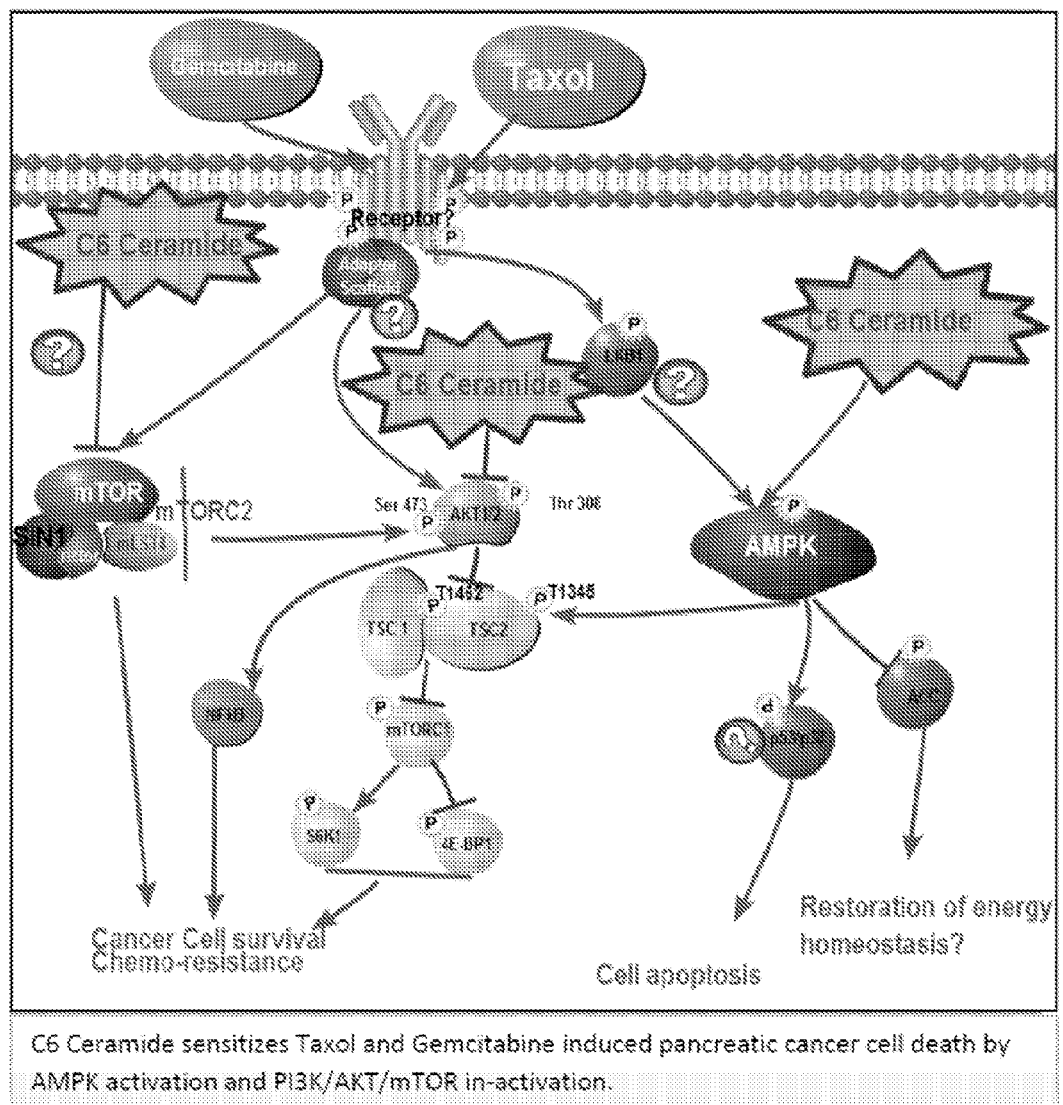
FIG. 6 shows a schematic outline of biological pathways affected by C6-ceramide.

In order to further explore this rational, various inhibitors of AKT/mTORC1 or ERK signaling pathways were used to assess the signaling pathways shown in FIGS. 5E-5F. The activation of AKT, mTORC1 or ERK signaling was blocked by various inhibitors. Thus, PI3K/AKT inhibitor LY 294002, mTORC1 inhibitor rapamycin, MEK/ERK inhibitor U0126, largely enhanced taxol and gemcitabine induced L3.6 cell death. Blocking P13K/AKT/mTORC1 and MEK/ERK signaling by adding both LY 294002 and U0126 caused a maximum effect on facilitating taxol or gemcitabine induced cell death, compared to blocking one signal pathway alone (FIG. 5E, arrow). These data indicate that activation of P13K/AKT/mTORC1 and MEK/ERK signaling pathways are a major cause of chemoresistance in treatment by anti-cancer agents, such as gemcitabine and taxol. C6-ceramide appears able to reverse the activation of these pathways to thereby potentiate the chemotherapeutic cytotoxic effects on the pancreatic cancer cells. A schematic outline of biological pathways affected by C6-ceramide is shown in FIG. 6.

Taken as a whole, it was found that activation of P13K/AKT/mTOR pathway is critical for the resistance against gemcitabine and paclitaxel induced pancreatic cancer cell death, since inhibitors of P13K/AKT/mTOR largely sensitized L3.6 pancreatic cancer cells due to gemcitabine and paclitaxel induced cell death (FIGS. 5E-5F). It was also determined that adding exogenous cell permeable C6-ceramide caused AKT and downstream mTORC1 inactivation. Interestingly paclitaxel or gemcitabine, which by itself had no effect on P13K/AKT activation, dramatically enhanced C6-ceramide induced AKT de-phosphorylation or inhibition (FIGS. 5A-5B). However, P13K/AKT/mTORC1 is not the only signaling pathway that is affected by exogenous cell permeable C6-ceramide treatment. ERK MAPK signaling is also inhibited by C6-ceramide treatment. Thus, adding paclitaxel or gemcitabine enhanced its inhibition on ERK activation (FIGS. 5A-5B). In L3.6 cells, ERK activation is a chemoresistant factor, since U0126, a well characterized MEK/ERK inhibitor, sensitized L3.6 cells to gemcitabine and paclitaxel induced cell death (FIG. 5F). These data demonstrate that P13K/AKT/mTOR inhibition, as well as ERK/MAPK inhibition, by C6-ceramide are likely the key mechanisms for the synergistic anti-cancer effects described herein.

Example 7

C6-Ceramide Sensitizes KRAS Mutated Pancreatic Cancer Cells to Cetuximab

Gemcitabine is the first-line chemotherapy for pancreatic cancer, with taxol as an alternative in experimental models. Chemotherapeutic agents cause side effects and cancer cells often fail to respond adequately due to acquisition of chemoresistance. Newer targeted therapies have been developed, such as cetuximab, which targets EGF receptors. However, with all of these agents, acquisition of KRAS mutations leads to marked resistance and decreased survival. Oncogenic KRAS mutations occur in 90% of patients with pancreatic cancer, rendering the protein constitutively active with the result that these tumors are highly aggressive and are resistant to chemotherapy.

Figure 7:
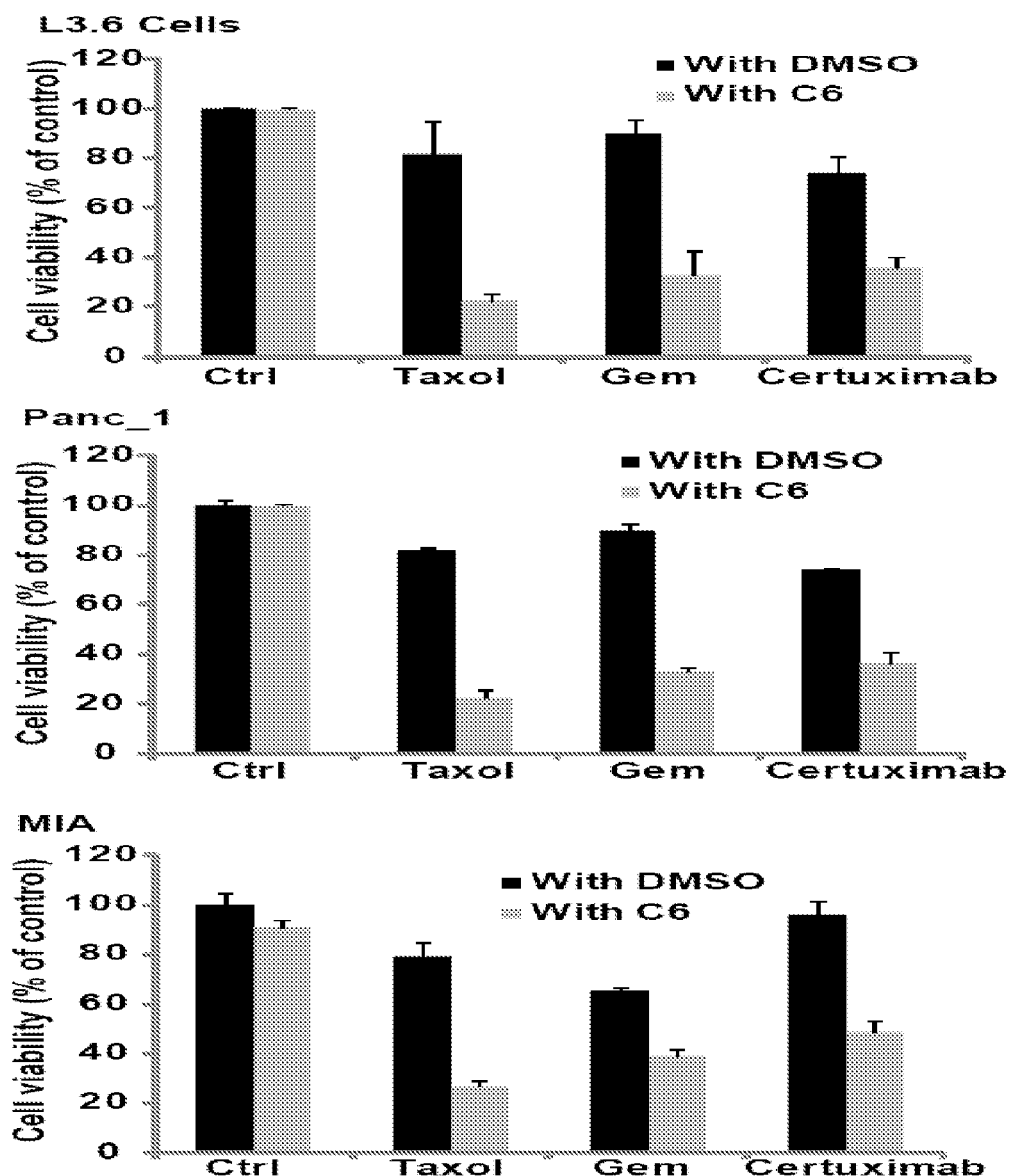
FIG. 7 shows that ceramide sensitizes KRAS mutated pancreatic cancer cells to cetuximab.

FIG. 7 demonstrates that C6-ceramide markedly sensitized PANC-1 and MIA PaCa-2 cells (both confirmed to harbor activating KRAS mutations), as well as L3.6 cells, to cetuximab.

Example 8

Combination of C6-Ceramide with Anti-Cancer Agents Inactivates Pro-Survival Signaling Pathways One of the most studied scaffold proteins for AKT activation is Gab1. Physical association between p85 and Gab1 is crucial in mediating the PI3K/AKT signaling pathway induced by a variety of stimuli. FIG. 5F shows that taxol induces Gab1 activation in wildtype but not Gab1 knockout MEFs. It is believed that that Gab1 is a key adaptor for taxol and gemcitabine induced PI3K/AKT/mTOR activation and chemoresistance response. To confirm this rationale, wildtype and Gab1 knockout MEFs and Gab1 siRNA can be used to test taxol and gemcitabine induced PI3K/AKT/mTOR and cell death. Interaction between Gab1 and p85 after Taxol and Gemcitabine treatment can also be tested in L3.6 cells.

In order to determine how anti-cancer agents, such as taxol and gemcitabine, induce mTORC1 activation, experiments can be performed to analyze AKT and TSC2, two key players for mTORC1 activation. It is believed that taxol and gemcitabine induced AKT activation mediates TSC2 phosphorylation, which inhibits TSC function as a negative regulator of mTORC1, leading to phosphorylation at S6K and 4E-BP1. AKT specific inhibitor AKTi and nonspecific inhibitor LY294002 are expected to block Taxol induced TSC2 phosphorylation (S1462) and mTORC1 activation. AKT1/2 deficiency will inhibit TSC2 phosphorylation and mTORC1 activation as well as enhance Taxol and Gemcitabine induced cancer cell death. It is expected that high basal level of mTORC1 activation in TSC2 knockout MEFs would be observed and that taxol and gemcitabine will not induce further activation of mTORC1. To further confirm the critical role of AKT/mTORC1 activation in taxol induced chemoresistance, inhibitors for AKT (AKT inhibitor II) and mTORC1 (rapamycin), with or without taxol and gemcitabine, can be given to pancreatic cancer model SCID mice. It is expected that those inhibitors enhance Taxol induced cell death in vivo, as indicated by lower mean tumor volume, lower tumor weight, longer survival rate, and the like in mice with those inhibitors plus taxol.

Based on the observation that taxol-induced AKT phosphorylation at Ser 473 is abolished in cells without Sin1 or mLST8, two key components of mTORC2, it is believed that mTORC2 is more sensitive to Taxol induced cell death and mTORC2 is important for Taxol to induce chemo-resistance. By using Sin1 and mLST8 deficiency MEF cells, it is expected that the mechanisms of phosphorylation of AKT at Ser 473 by taxol will be identified. It is further expected that taxol-induced AKT phosphorylation at Ser 473 will be abolished in either SIN1 or mLST8 knockout MEFs.

In addition, it has been demonstrated herein that taxol alone is able to induce moderate AMPK activation in pancreatic cell line. For example, AICAR, an AMPK activator, was able to enhance Taxol induced cell death (FIG. 4C), while AMPK inhibitor Compound C inhibits it (FIG. 4D). C6-ceramide dramatically enhances Taxol induced AMPK and its downstream signaling ACC phosphorylation in L3.6 cell line (FIG. 4A), which likely serves as another key mechanism to explain the synergistic effects of C6-ceramide plus chemotherapy drugs for inducing cancer cell death, since AMPK plays a critical role in tumor-genesis and AMPK activation mediates cancer cell death in a mTOR dependent and independent manner. To further confirm the requirement of AMPK activation in this synergistic effect, siRNA directed against AMPK can be used. It is expected that the synergistic effect would be impaired in AMPK knockdown cells. L3.6 cells can be transfected with TSC2 site-specific mutation plasmids to generate TSC2 dominant negative cells and it is expected that taxol and ceramide would induce AMPK activation but with less mTORC1 inhibition in TSC2 dominant cells. In addition, it is expected that dominant negative cells would be less sensitive to induced cell death by a combination of taxol and C6-ceramide.

Taxol directly induces reactive oxygen production (ROS) production and mitochondria stress, ROS is known as a strong AMPK activator. LKB1 is well-recognized AMPK Kinase. Accordingly, the requirement for ROS production in AMPK activation by taxol can be assayed. L3.6 cells with or without antioxidants PDTC or NAC pretreatment can be treated with taxol, ceramide or taxol plus ceramide and ROS production, LKB1/AMPK/ACC activation, and L3.6 cell death can be tested. It is expected that ceramide will enhance taxol induced ROS production and LKB1 activation, NAC and PDTC impaired ROS production, LKB1/AMPK/ACC activation, and cell death induced either by taxol and taxol plus ceramide.

Regarding the relationship between ceramide and KRAS signaling, it has been demonstrated herein that C6-ceramide sensitizes cancer cells to cetuximab to thereby indicate an interaction with the KRAS pathway. Oncogenic Kras stimulates a signaling cascade: Raf/MEK/ERK with subsequent effects on NF-kB and PI3K/AKT, survival pathways along with the network effects on jun c, Bcl-2, Bcl-xL. Assessment of in vitro effects on well-known targets in these pathways can include MTT or XTT cytotoxic assay, caspase 8, and 3, and Tunel assays. The detailed baseline effects of the KRAS pathway can be evaluated on the anti-tumor effects of C6-ceramide and selected drug combinations, such as paclitaxel (taxol) (commonly used in variety of cancers, gemcitabine (currently accepted agent in therapy of pancreatic cancer), and cetuximab (currently used for colorectal and head and neck cancers).

The effect of known RAS inhibitors on the C6-ceramide anti-cancer effects can also be assessed. These can include the farnesyl/transferase inhibitors: farnesylthiosalicylic acid (Salirasib; Rotblat et al. (2008) Methods Enzymol. 439:467-489, and Tipifarnib (farnesy/protein transferase inhibitor (R115777; McDonald et al. (2005) Invest. New Drug 23:485-487. Similarly, molecular biology approces targeting the KRAS signaling network can be taken by, for example, transfecting cells with pre-let 7a microRNA or Lin 28 siRNA, both of which decrease the expression of KRAS protein (Kim et al. (2010) Int. J. Radiat. Oncol. Biol Phys. 76:1-5. Alternatively, mutant KRAS can be targeted directly with an siRNA (Zhu et al. (2006) Cancer Biol Ther. 5:1693-1698).

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) on the world wide web at tigr.org and/or the National Center for Biotechnology Information (NCBI) on the world wide web at ncbi.nlm.nih.gov.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method for treating colorectal cancer having an activating KRAS mutation, comprising administering to a mammal a pharmaceutically acceptable formulation comprising (a) an effective amount of C6-ceramide; (b) an effective amount of 5-fluorouracil; (c) an effective amount of oxaliplatin; and (d) an effective amount of cetuximab.

2. The method of claim 1, wherein the mammal is a human.

3. The method of claim 1, wherein the activating KRAS mutations is a human KRAS polypeptide having a mutation selected from the group consisting of G12C, G12A, G12D, G12R, G12S, G12V, G13C, and G13D.

4. The method of claim 1, wherein the administration route is selected from the group consisting of parenteral and anal.

\* \* \* \* \*